US008697872B2

(12) United States Patent
Wang et al.

(10) Patent No.: US 8,697,872 B2
(45) Date of Patent: Apr. 15, 2014

(54) BORON COMPOUNDS AND USES THEREOF

(75) Inventors: Suning Wang, Kingston (CA); Hazem Y. S. Amarne, Windsor (CA); Yingli Rao, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 0 days.

(21) Appl. No.: 13/433,865

(22) Filed: Mar. 29, 2012

(65) Prior Publication Data

US 2012/0253044 A1    Oct. 4, 2012

Related U.S. Application Data

(60) Provisional application No. 61/470,046, filed on Mar. 31, 2011.

(30) Foreign Application Priority Data

Mar. 31, 2011    (CA) ..................................... 2735531

(51) Int. Cl.
*C07F 5/02*      (2006.01)
*C07D 235/04*   (2006.01)

(52) U.S. Cl.
USPC ........................................... 546/13; 548/110

(58) Field of Classification Search
USPC ........................................... 548/110; 546/13
See application file for complete search history.

(56) References Cited

U.S. PATENT DOCUMENTS

| | | | |
|---|---|---|---|
| 4,990,287 A | 2/1991 | Bennion et al. | |
| 5,480,749 A | 1/1996 | Green | |
| 5,539,100 A | 7/1996 | Wasielewski et al. | |
| 5,932,393 A * | 8/1999 | Cunningham et al. | 430/281.1 |
| 6,034,193 A | 3/2000 | Henry et al. | |
| 6,312,835 B1 | 11/2001 | Wang | |
| 6,438,298 B1 | 8/2002 | Matsui et al. | |
| 6,500,569 B2 | 12/2002 | Wang | |
| 6,807,138 B1 | 10/2004 | Jamail et al. | |
| 7,432,027 B2 | 10/2008 | Chopra et al. | |
| 7,521,159 B2 | 4/2009 | Iftime et al. | |
| 7,989,089 B2 | 8/2011 | Wang | |
| 2003/0174560 A1 | 9/2003 | Dahmen et al. | |
| 2003/0213942 A1 | 11/2003 | Kim et al. | |
| 2004/0265629 A1 | 12/2004 | Wang | |
| 2006/0036114 A1 | 2/2006 | Wang | |
| 2006/0291833 A1 | 12/2006 | Timans | |

FOREIGN PATENT DOCUMENTS

| | | |
|---|---|---|
| CN | 101268159 A | 9/2008 |
| CN | 100427479 C | 10/2008 |
| CN | 201194534 Y | 2/2009 |
| EP | 1487936 B1 | 9/2006 |
| JP | 3994617 | 10/2007 |
| WO | WO 96/13751 | 5/1996 |
| WO | WO 00/77559 | 12/2000 |
| WO | WO 2006/003574 | 1/2006 |
| WO | WO2007/018301 A1 | 2/2007 |
| WO | WO 2008/131392 | 10/2008 |
| WO | WO 2009/141295 | 11/2009 |

OTHER PUBLICATIONS

Amarne, H. et al.: Photoisomerization of 1-phenyl-2-(pyridin-2-yl)indole BMes2: the dark isomer. Organonmetallics, vol. 30, pp. 665-668, 20111.*
Amarne, H. et al.: Steric and electronic influence on photochromic switching of N,C-chelate four-coordinate organoboron compounds. Chem. Eur. J. vol. 16, pp. 4750-4761, 2010.*
Rao, Y-L. et al.: Reversible intramolecular C-C bond formation/breaking and color switching mediated by a N,C-chelate in (2-ph-py)BMes2 and (5-BMes2-2-ph-py)BMes2. J. Am. Chem. Soc., vol. 130, pp. 12898-12900, 2008.*
Wakamiya, A. et al.: Intramolecular B-N coordination as a scaffold for electron-transporting materials: synthesis and properties of boryl-substituted thienylthiazoles. Angew. Chem. Int. Ed., vol. 45, pp. 3170-3173, 2006.*
Berkovic, G. et al., "Spiropyrans and Spirooxazines for Memories and Switches", Chem. Rev., 100, 1741-1753, (2000).
Corns, S.N. et al., "Industrial organic photochromic dyes", Colouration Technology, 125, 249-261, (2009).
Cox, M.E., "Oxygen Diffusion in Poly(dimethyl Siloxane) using Fluorescence Quenching. I. Measurement Technique and Analysis", Journal of Polymer Science: Part A: Polymer Chemistry, vol. 24, 621-636 (1986).
Kobatake, S. et al., "Photochromism", Annu. Rep. Prog. Chem., Sect. C, 99, 277-313 (2003).
Lee, S-K, et al., "Photostable Optical Oxygen Sensing Material: Platinum Tetrakis(pentafluorophenyl)porphyrin Immobilized in Polystyrene", Analytical Communications, Jun. vol. 34, 185-188, (1997).
Mennig, M., et al., "Development of fast switching photochromic coatings on transparent plastics and glass", Thin Solid Films 351, 230-234, (1999).
Mills, A., et al., "Nanocrystalline Sn02-based, UVB-activated, colourimetric oxygen indicator", Sensors and Actuators B 136, 344-349, (2009).
Rao, Y-L., et al., "Four-Coordinate Organoboron Compounds with a pi-Conjugated Chelate Ligand for Optoelectronic Applications," Inorganic Chemistry, vol. 50, 12263-12274 (2011).
Rao, Y-L., et al., "Photochromic four-coordinate N,C-chelate boron compounds," Coordination Chemistry Reviews, vol. 256, 759-770 (2012).

(Continued)

*Primary Examiner* — Charanjit Aulakh
(74) *Attorney, Agent, or Firm* — Angela Lyon; Carol Miernicki Steeg; Emma Saffman

(57) ABSTRACT

Organoboron compounds are described that upon exposure to light absorb light and isomerize and form a dark-colored isomer. The dark-colored isomer converts back to the colorless isomer upon removal of light, or exposure to oxygen or heat. Such compounds can be added into polymeric matrices such as films. These compounds are suitable for UV-blocking, UV-detecting, and for oxygen-sensing applications. Uses include UV-blocking windows, sunglasses, and as indicators in packaging such as food packaging.

20 Claims, 18 Drawing Sheets

(56) References Cited

OTHER PUBLICATIONS

Amberg-Schwab, S., "Development of oxygen scavenger and indicator systems for the enhancement and indication of food quality", Fraunhofer ISC Annual Report, 32-35, 2006.

Rao, Y-L., et al., "Reversible Intramolecular C-C Bond Formation/Breaking and Color Switching Mediated by a N,C-Chelate in (2-ph-py)BMes2 and (5-BMes2-2-ph-py)BMes2" JACS, 130, 12898-12900, (2008).

Baik, C. et al., "Enhancing the Photochemical Stability of N,C-Chelate Boryl Compounds: C-C Bond Formation versus C=C Bond cis, trans-Isomerization", JACS, 131, 14549-14559, (2009).

Amarne, H., et al., "Steric and Electronic Influence on Photochromic Switching of N,C-Chelate Four-Coordinate Organoboron Compounds", Chemistry Eur. J., 16, 4750-4761, (2010).

Murphy, S., et al., "Single Boryl Isomerization in Silyl-Bridged Photochromic Diboryl Dyes", Organic Letters, vol. 12, No. 22, 5266-5269, (2010).

Baik, C. et al., "Switching of a Single Boryl Center in pi-Conjugated Photochromic Polyboryl Compounds and its Impact on Fluorescence Quenching", Angew. Chem. Int. Ed., 49, 8224-8227, (2010).

Zhou, Z. et al., "Modulation of the Photochromic Property in an Organoboron-based diarylethene by a fluoride ion", Organic Letters, vol. 8, No. 18, 3911-3914, (2006).

Ding, Y. et al., "A simple, low waste and versatile procedure to make polymer electrochromic devices", J. Mater. Chem., 21, 11873-11878, (2011).

\* cited by examiner compound 10   compound 10a compound 14

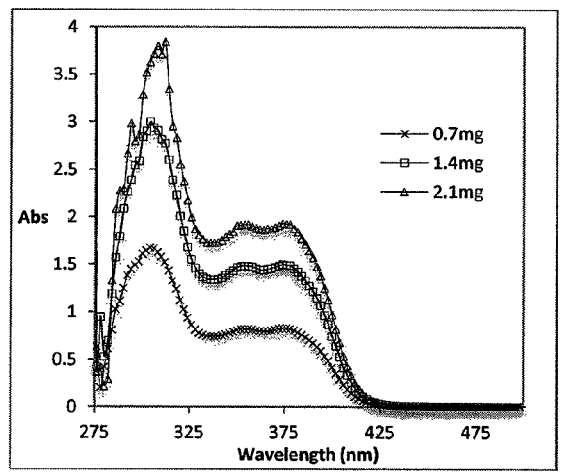
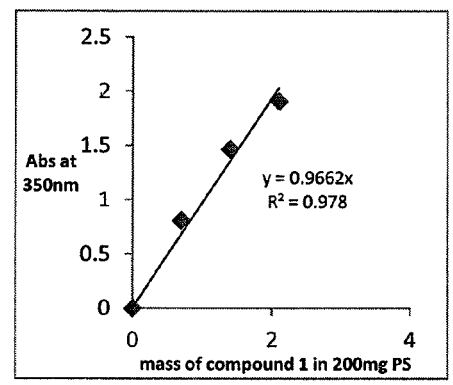
Figure 5A                 Figure 5B
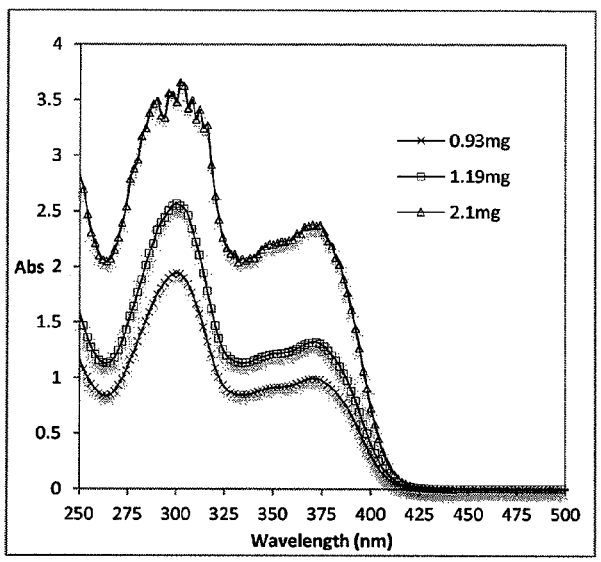
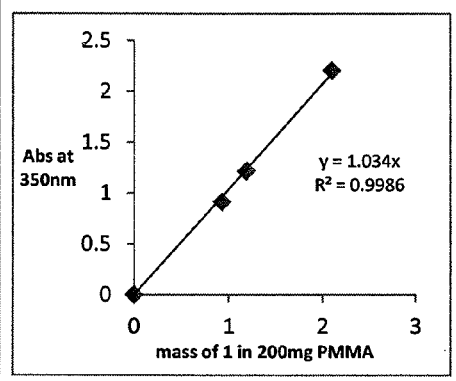
Figure 6A                 Figure 6B

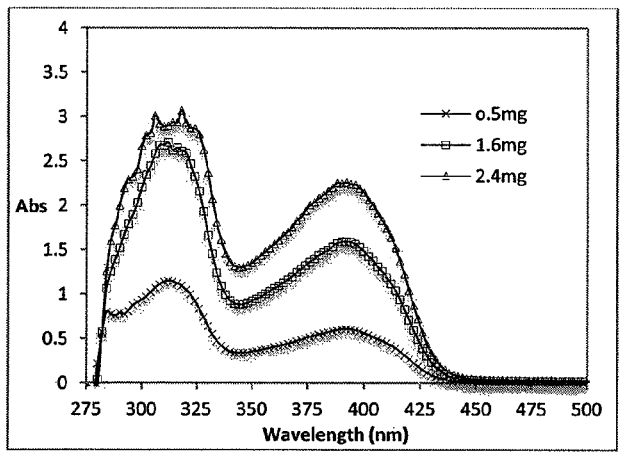
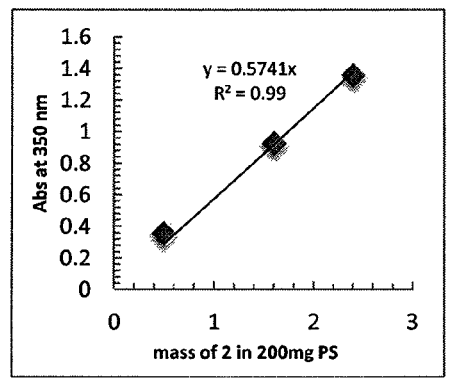
Figure 7A Figure 7B
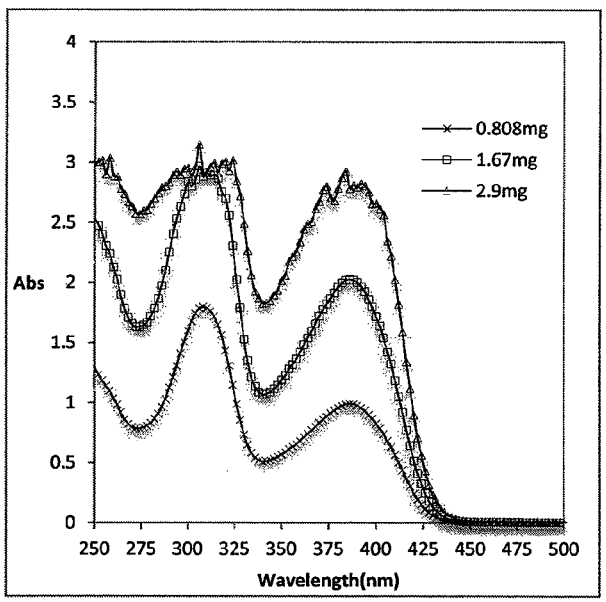
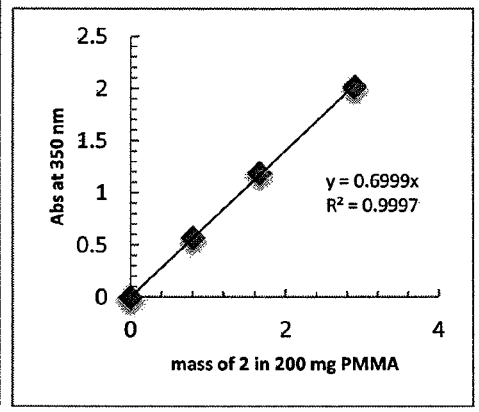
Figure 8A Figure 8B

BORON COMPOUNDS AND USES THEREOF

CROSS-REFERENCE TO RELATED APPLICATIONS

This application claims the benefit of the filing date of U.S. Provisional Patent Application No. 61/470,046 filed on Mar. 31, 2011, the contents of which are incorporated herein by reference in their entirety.

FIELD OF THE INVENTION

The field of the invention is four-coordinate boron compounds. More specifically, the field of the invention is compounds that are photochromic and so can change color upon exposure to light (UV or visible) and can reverse color when in the absence of light, when heated, and/or when irradiated by light of a different energy.

BACKGROUND OF THE INVENTION

Photochromic and photo-thermal chromic dyes such as spiropyrans, spirooxazines, naphthopyrans and dithienylethenes (DTE) have attracted great attention due to their applications in smart windows and ophthalmic eyewear (see Berkovic, G., et al., *Chem. Rev.* 2000, 100:1741, Kobatake, S. et al., *Annu. Rep. Prog. Chem.*, Sect. C 2003, 99:277, Crano, J. C.; et al., *J. Organic Photochromic and Thermochromic Compounds*; Plenum Press: New York, 1999, Corns, S, N. et al., *Color. Tech.* 2009, 125:249). Modification of such photochromes could allow fine-tuning of their photochromic properties. However, development of a novel thermally reversible photochromic dye with different switching kinetics, thermal stability, and coloration is needed to allow development of new switching devices and applications.

SUMMARY OF THE INVENTION

It is an object of certain embodiments of the present invention to provide four-coordinate boron compounds. In some embodiments, such compounds are photochromic and so they are suitable for use in photochromic material such as memory devices (e.g., optical data storage devices, electronic paper, switchable UV blocker or shield such as smart window). Other objects and advantages of the present invention will become apparent from the disclosure herein.

An aspect of the invention provides a compound of general formula (A):

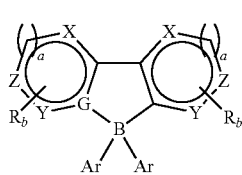

(A)

wherein
B is boron;
G is nitrogen, sulfur, substituted or unsubstituted carbon, or oxygen;
a is zero or one;
X, Y and Z are independently oxygen, sulfur, substituted or unsubstituted nitrogen, or substituted or unsubstituted carbon;
Ar is independently a substituted or unsubstituted aryl moiety wherein at least one of the two Ar moieties is bi-, tri-, tetra-, or penta-substituted aromatic moiety that has substitutents located at least in the two ortho positions relative to the boron-Ar bond, and optionally there are substituents located in the meta and para positions as well;
R is a substituent; and
b is a number from 0 to 5;
wherein substituents include aliphatic groups (including alkyl, alkenyl, alkynyl), alkoxyl, silyl, siloxy, aryl, B(aliphatic)(aryl), B(aryl)$_2$, or any combination thereof, wherein a substituent may be further substituted, and wherein two substituents can join to form a fused aryl ring.

In an embodiment of the above aspect, Ar is independently a substituted or unsubstituted aromatic moiety wherein at least one of the two Ar moieties is a bi-, tri-, tetra-, or penta-substituted aromatic moiety that has substitutents located in the two ortho positions relative to the boron-Ar bond.

In an embodiment of the above aspect when X is carbon, at least one of Z and Y is a heteroatom. In another embodiment of the above aspect when one of X, Y and Z is nitrogen, another one of X, Y and Z is sulfur or oxygen, and the remaining one of X, Y and Z is carbon. In another embodiment of the above aspect when X is oxygen or sulfur, both Y and Z are carbon. In an embodiment of the above aspect when one of X, Y and Z is nitrogen, the remaining two of X, Y and Z are carbon. In an embodiment of the above aspect when two of X, Y and Z are nitrogen, the remaining one of X, Y and Z is carbon. In yet another embodiment of the above aspect all three of X, Y and Z are nitrogen. In some embodiments of compounds of general formula (A), when a is one in both instances, G is nitrogen, X, Y, and Z are carbon, then when one b is zero the other b is not zero. In some embodiments, when a is one in both instances, and for the ring that includes G, G is nitrogen, b is one, and R is —B(Mes)$_2$, —C≡C-phenyl, —CH(═O), or —C≡C-phenyl; then the other b is not zero. In some embodiments of compounds of general formula (A), when a is 1 in both instances and for the ring that includes G, b is one and R is B(Mes)$_2$, then the other b is not zero.

In an embodiment of the above aspect the compound of general formula (A) is: compound 1, compound 2, compound 8, compound 9, compound 10, compound 11, compound 12, compound 13, or compound 14. In certain embodiments of the above aspect Ar is 1,3,5-mesityl. In some embodiments of the above aspect R is B(mesityl)$_2$. In some embodiments of the above aspect, G is carbon.

A second aspect of the invention provides a compound of general formula (B):

(B)

wherein
B is boron;
G is nitrogen, sulfur, substituted or unsubstituted carbon, or oxygen;
a is zero or one;
X, Y and Z are independently oxygen, sulfur, substituted or unsubstituted nitrogen, or substituted or unsubstituted carbon;

E is substituted or unsubstituted nitrogen or substituted or unsubstituted carbon;

Ar is independently a substituted or unsubstituted aryl moiety wherein at least one of the two Ar moieties is bi-, tri-, tetra-, or penta-substituted aromatic moiety that has substitutents located at least in the two ortho positions relative to the boron-Ar bond, and optionally there are substituents located in the meta and para positions as well;

R is a substituent; and b is a number from 0 to 5;

wherein substituents include aliphatic groups, alkoxyl, silyl, siloxyl, aryl, B(aliphatic)(aryl), B(aryl)$_2$, or any combination thereof, wherein a substituent may be further substituted, and wherein two substituents can join to form a fused aryl ring.

In an embodiment of the second aspect, Ar is independently a substituted or unsubstituted aromatic moiety wherein at least one of the two Ar moieties is a bi-, tri-, tetra-, or penta-substituted aromatic moiety that has substitutents located in the two ortho positions relative to the boron-Ar bond.

In an embodiment of the second aspect, G is carbon. In another embodiment of the second aspect, G is carbon, E is nitrogen, Y in the ring containing G is nitrogen, and Y in the other ring is carbon. In certain embodiments of the second aspect, wherein a is 0. In some embodiments of the second aspect, a is 1 in the ring containing G, and a is 0 in the other ring. In some embodiments of the second aspect, b is 1 in the ring containing G, and b is 0 in the other ring. In some embodiments of the second aspect, b is 3 in the ring containing G, and b is 0 in the other ring. In certain embodiments of the second aspect, b is 3 in the ring containing G, and two substituents join together to form a fused aryl ring.

In an embodiment of the second aspect, Ar is 1,3,5-mesityl. In an embodiment of the second aspect, the compound of general formula (B) is: compound 15 or compound 16.

A third aspect of the invention provides a compound of general formula (C):

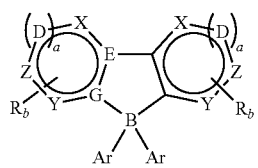

(C)

wherein

B is boron;

G is nitrogen, sulfur, substituted or unsubstituted carbon, or oxygen;

D is substituted or unsubstituted nitrogen, sulfur, substituted or unsubstituted carbon, or oxygen;

a is zero or one;

X, Y and Z are independently oxygen, sulfur, substituted or unsubstituted nitrogen, or substituted or unsubstituted carbon;

E is substituted or unsubstituted nitrogen or substituted or unsubstituted carbon;

Ar is independently a substituted or unsubstituted aryl moiety wherein at least one of the two Ar moieties is bi-, tri-, tetra-, or penta-substituted aromatic moiety that has substitutents located at least in the two ortho positions relative to the boron-Ar bond, and optionally there are substituents located in the meta and para positions as well;

R is a substituent; and b is a number from 0 to 5;

wherein substituents include aliphatic groups, alkoxyl, silyl, siloxyl, aryl, B(aliphatic)(aryl), B(aryl)$_2$, or any combination thereof, wherein a substituent may be further substituted, and wherein two substituents can join to form a fused aryl ring.

In an embodiment of the third aspect, Ar is independently a substituted or unsubstituted aromatic moiety wherein at least one of the two Ar moieties is a bi-, tri-, tetra-, or penta-substituted aromatic moiety that has substitutents located in the two ortho positions relative to the boron-Ar bond.

A fourth aspect of the invention provides a compound of general formula (D):

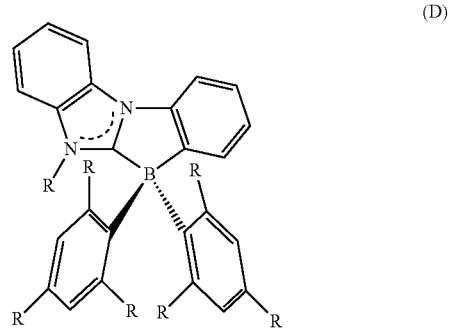

(D)

wherein R is H, alkyl, aryl, or BAr$_2$. In an embodiment of the fourth aspect, R is methyl and the compound of general formula (D) is compound 15:

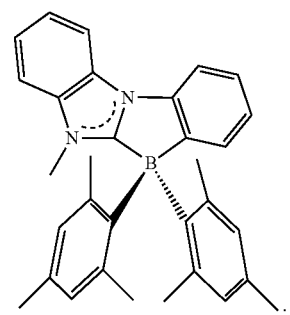

15

A fifth aspect of the invention provides a compound of general formula (E):

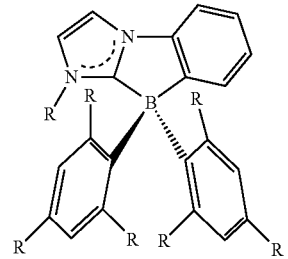

(E)

wherein R is H, alkyl, aryl, or BAr$_2$. In an embodiment of the fifth aspect, R is methyl and the compound is compound 16:

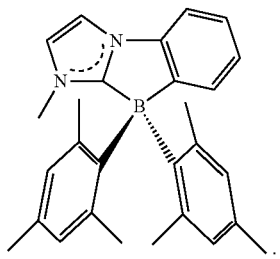

In certain embodiments of the above aspects, the compound is photochromic. In some embodiments of the above aspects, the compound's reactivity is controlled or transformed when irradiated by light.

In respective other aspects the invention provides methods of making a compound of general formula (A), (B), (C), (D) or (E). In an embodiment, a method of making a compound of general formula (A) comprises reacting a chelate ligand in a toluene solution at about −78° C. with either n-butyl lithium or lithium di(isopropyl)amide, adding $BAr_2halo$, and warming the solution to ambient temperature.

In respective other aspects the invention provides photochromic materials comprising a compound of general formula (A), (B), (C), (D) or (E). In some embodiments of these aspects, the material is a transparent medium that turns to a dark color when exposed to light. In certain embodiments, the medium is glass, plexiglass, plastic, etc. and may include a window, eyewear (glasses and/or sunglasses), or automobile windshield.

In yet other aspects the invention provides methods of producing an image in a material that comprises a compound of general formula (A), (B), (C), (D) or (E), comprising exposing a certain location(s) on the material to light, preventing another location(s) on the material from light-exposure, and obtaining a pattern of dark-colored and colorless areas on the material that is analogous to the pattern of exposure/non-exposure. In some embodiments of this aspect, the light is UV light.

In other aspects the invention provides methods of sensing oxygen, comprising exposing a compound of general formula (A), (B), (C), (D) or (E) to an atmosphere for testing, and detecting isomerization of the compound. In certain embodiments of these aspects the detecting comprises detecting a change in the compound's fluorescence, absorbance, color, or a combination thereof. In some embodiments of these aspects the compound is in a polymeric film. In some embodiments of these aspects the film is disposed in food packaging.

In other aspects the invention provides a molecular switch comprising a compound of general formula (A), (B), (C), (D) or (E), wherein the compound can be switched between two isomeric states by exposure to and removal of light. In some embodiments of these aspects the compound is present in memory media. In certain embodiments of these aspects the compound is present in a polymeric matrix. The polymeric matrix comprises PDMS, PS, PE, PVK, PMMA, EVOH, or a combination thereof.

Other aspects of the invention provide a circuit comprising a molecular switch of the above aspects.

Yet other aspects of the invention provide methods of UV blocking comprising adding a compound of general formula (A), (B), (C), (D) or (E) to a oxygen-impenetrable transparent medium, such that when UV light shines on the medium, the compound isomerizes and blocks UV from penetrating the medium.

Other aspects of the invention provide methods of UV blocking comprising adding a compound of general formula (A), (B), (C), (D) or (E) to a oxygen-impenetrable transparent medium, such that when UV light shines on the medium, the compound absorbs UV light, isomerizes, and UV light is inhibited from penetrating the medium. In some embodiments of these aspects upon exposure to UV light, the compound changes color.

Other aspects of the invention provide a composition comprising a compound of general formula (A), (B), (C), (D) or (E), and a polymer. In some embodiments of these aspects the polymer is poly(dimethylsiloxane), polystyrene, polyethylene, polyvinylcarbazole, poly(methyl methacrylate), or a copolymer of poly(ethylene-co-vinyl alcohol).

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which:

FIG. 5A is a plot of absorbance versus wavelength and shows the absorption spectra for PS films doped by different amounts (as specified) of compound 2.

FIG. 5B is diagram showing the linear dependence of the absorbance at 350 nm with the amount of compound 2 doped in PS.

FIG. 6A is a plot of absorbance versus wavelength and shows the absorption spectra for polymethylmethacrylate (PMMA) films doped by different amounts (as specified) of compound 2.

FIG. 6B is a plot of absorbance versus mass of compound 2 in 200 mg PMMA and shows a linear dependence of the absorbance at 350 nm with the amount of compound 2 doped in PMMA.

FIG. 7A is a plot of absorbance versus wavelength and shows the absorption spectra for PS films doped by different amounts (as specified) of compound 8.

FIG. 7B is a plot of absorbance versus mass of compound 8 in 200 mg PS and shows a linear dependence of the absorbance at 350 nm with the amount of compound 8 doped in PS.

FIG. 8A is a plot of absorbance versus wavelength and shows the absorption spectra for PMMA films doped by different amounts (as specified) of compound 8.

FIG. 8B is a plot of absorbance versus mass of compound 8 in 200 mg PMMA and shows a linear dependence of the absorbance at 350 nm with the amount of compound 8 doped in PMMA.

DETAILED DESCRIPTION OF PREFERRED EMBODIMENTS

Definitions

Figure 1A:
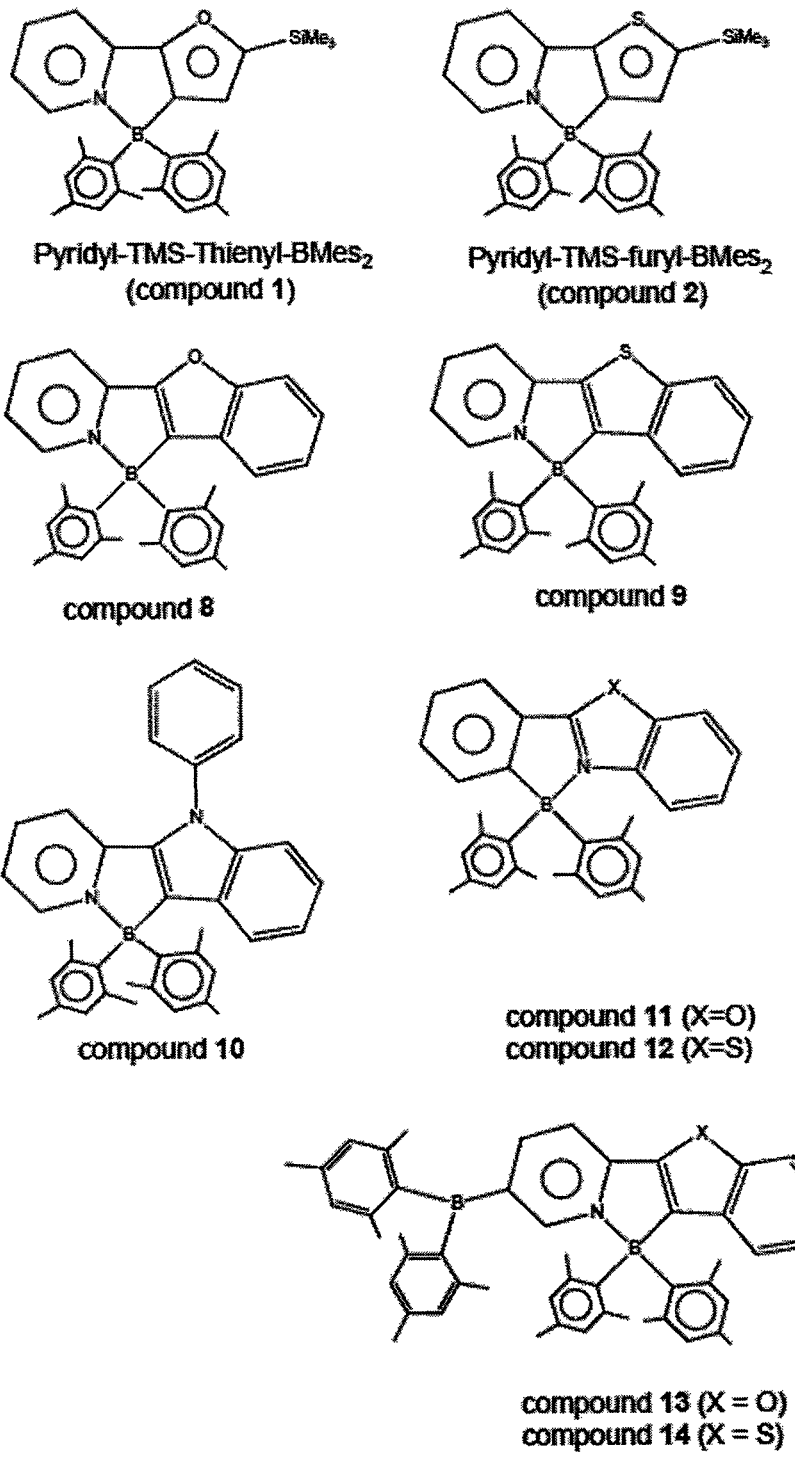
FIG. 1A shows structural formulae for compounds described herein.

As used herein, the term "photochromic" means a reversible transformation of a chemical species between two forms by absorption of electromagnetic radiation where the two forms have different absorption spectra. Trivially, for some embodiments, this term can be described as turning dark when exposed to a light source (e.g., natural sunlight) and returning to its normal transparency with the removal of the light source. An example of an object that changes colour in such conditions is sunglasses that darken when sunlight becomes brighter.

As used herein, the term "dative bond" means a covalent bond in which both shared electrons are furnished by the same atom.

As used herein, the term "halo" means a halogen atom and may include a halide (e.g., Cl, Br, I, F).

As used herein, the term "poly(dimethylsiloxane)" is abbreviated as PDMS.

As used herein, the term "polystyrene" is abbreviated as PS.

As used herein, the term "poly(methyl methacrylate)" is abbreviated as PMMA.

As used herein, the term "poly(ethylene-co-vinyl alcohol)" is abbreviated as EVOH.

As used herein, the term "n-butyl lithium" is abbreviated nBuLi. As used herein, the term LDA means lithium di(isopropyl)amide.

As used herein, the term "aliphatic" includes alkyl, alkenyl and alkynyl. An aliphatic group may be substituted or unsubstituted. It may be straight chain, branched chain or cyclic.

As used herein, the term "aryl" includes heteroaryl and may be substituted or unsubstituted.

As used herein, the term "unsubstituted" refers to any open valence of an atom being occupied by hydrogen. Also, if an occupant of an open valence position on an atom is not specified, then it is hydrogen.

As used herein, the term "substituted" refers to a structure having one or more substituents.

As used herein, the term "chelate ligand" means a chemical moiety that binds to a central atom via more than one bond (bi- or multi-dentate).

As used herein, the term "mesityl" means 2,4,6-trimethylphenyl.

As used herein, the term "silyl" means $—Si(R)_3$ where R is an aliphatic moiety.

As used herein, the term "siloxy" means $—Si(OR)_3$, and $—Si(OR)_x(R')_y$ where R, and R' are aliphatic moieties, and where x and y are numbers from 0 to 3 and x+y=3.

Embodiments

A four-coordinate organoboron compound based on a ppy-BMes$_2$ (ppy=2-phenylpyridine, Mes=mesityl) chromophore can undergo a thermally reversible photoisomerization process accompanied by a distinct color change from either colorless or light yellow to dark blue or green (see Wang, S., et al., J. Am. Chem. Soc. (2008) 130:12898; Wang, S. et al., J. Am. Chem. Soc. (2009) 131:14549; Wang, S. et al., Chem. Eur. J. (2010) 16:4750; Wang, S. et al., Angew. Chem. Intl. Ed. (2010) 49:8224; and Wang S., et al., Org. Lett., (2010) 12:5266.) However, the ppy-BMes$_2$ system is slow to switch from its light-colored state to its dark-colored state.

To overcome this limitation, a new class of photochromic organoboron compounds has been developed and is described herein. This new class of photochromic organoboron compounds has a heterocyclic group (e.g., indolyl, thienyl, or furyl) in place of the phenyl ring of the ppy. In addition, the pyridyl ring in the original ppy chelate may be replaced by either a non-heterocyclic aryl ring or a non-pyridyl heterocyclic ring. Thus an aspect of the invention provides a photochromic, neutral (uncharged) compound having a four-coordinate boron atom, wherein the four bonds include three boron-carbon bonds and one boron-nitrogen dative bond. Such compounds have general formula (A) as shown below:

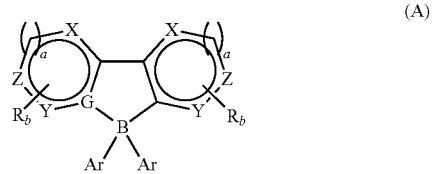

(A)

wherein
B is boron;
G is nitrogen, sulfur, substituted or unsubstituted carbon or oxygen;
a is zero or one;
X, Y and Z are independently oxygen, sulfur, substituted or unsubstituted nitrogen, or substituted or unsubstituted carbon;

Ar is independently a substituted or unsubstituted aryl moiety wherein at least one of the two Ar moieties is bi-, tri-, tetra-, or penta-substituted aromatic moiety that has substitutents located at least in the two ortho positions relative to the boron-Ar bond, and optionally there are substituents located in the meta and/or para positions as well;

R is a substituent;

b is a number from 0 to 5;

wherein substituents include aliphatic groups (which includes alkyl, alkenyl, alkynyl), alkoxyl, silyl, siloxyl, aryl, B(aliphatic)(aryl), B(aryl)$_2$, or any combination thereof, wherein a substituent may be further substituted, and wherein two substituents can join to form a fused aryl ring. As defined above, aryl includes heteroaryl.

In some embodiments, the Ar group in general formula (A) is 1,3,5-mesityl.

For each boron-carbon bond of general formula (A), the boron atom donates one electron and the carbon atom donate the other electron to make up a two electron bond. For the boron-nitrogen bond of general formula (A), a dative bond is formed by the nitrogen atom donating its lone pair of electrons. Due to the dative nature of the boron-nitrogen bond, compounds of general formula (A) are neutral (uncharged).

In certain embodiments, X is carbon, and at least one of Z and Y is a heteroatom.

In certain embodiments of general formula (A), one of X, Y and Z is nitrogen, another one of X, Y and Z is sulfur or oxygen, and the remaining one of X, Y and Z is carbon. In some embodiments of general formula (A), X is oxygen or sulfur, and both Y and Z are carbon. In some embodiments of general formula (A), one of X, Y and Z is nitrogen, and the remaining two of X, Y and Z are carbon. In some embodiments, two of X, Y and Z are nitrogen, and the remaining one of X, Y and Z is carbon. In some embodiments of general formula (A), all three of X, Y and Z are nitrogen.

In some embodiments of compounds of general formula (A), a is one in both instances, G is nitrogen, X, Y, and Z are carbon, one b is zero and the other b is not zero.

In some embodiments, when a is one in both instances, and for the ring that includes G, G is nitrogen, b is one, and R is —B(Mes)$_2$, —C≡C-phenyl, —CH(═O), or —C≡C-phenyl; then the other b is not zero.

In some embodiments of compounds of general formula (A), a is 1 in both instances and for the ring that includes G, b is one and R is B(Mes)$_2$; then the other b is not zero.

In some embodiments of compounds of general formula (A), a is 1 for the ring that includes G and 0 for the other ring, and G is carbon.

Compounds of general formula (A) include compounds whose structural formulae are shown in FIG. 1.

In an embodiment, organoboron compounds have the structure of general formula (B) as shown below:

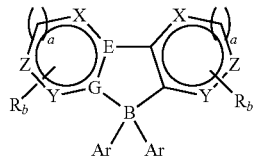

(B)

wherein

B is boron;

G is nitrogen, sulfur, substituted or unsubstituted carbon, or oxygen;

a is zero or one;

X, Y and Z are independently oxygen, sulfur, substituted or unsubstituted nitrogen, or substituted or unsubstituted carbon;

E is substituted or unsubstituted nitrogen, or substituted or unsubstituted carbon;

Ar is independently a substituted or unsubstituted aryl moiety wherein at least one of the two Ar moieties is bi-, tri-, tetra-, or penta-substituted aromatic moiety that has substitutents located at least in the two ortho positions relative to the boron-Ar bond, and optionally there are substituents located in the meta and/or para positions as well;

R is a substituent; and b is a number from 0 to 5;

wherein substituents include aliphatic groups, alkoxyl, silyl, siloxyl, aryl, B(aliphatic)(aryl), B(aryl)$_2$, or any combination thereof, wherein a substituent may be further substituted, and wherein two substituents can join to form a fused aryl ring.

In some embodiments, compounds of general formula (B) are photochromic.

In some embodiments of compounds of general formula (B), G is carbon. In some embodiments, E is nitrogen. In some embodiments, G is carbon and E is nitrogen.

In some embodiments of compounds of general formula (B), G is carbon, E is nitrogen, Y in the ring containing G is nitrogen, and Y in the other ring is carbon.

In some embodiments of compounds of general formula (B), a is 0. In some embodiments of compounds of general formula (B), a is 1 for the ring containing G, and a is 0 for the other ring.

In some embodiments of compounds of general formula (B), Ar is 1,3,5-mesityl.

In some embodiments of compounds of general formula (B), b is 1 for the ring containing G, and b is 0 for the other ring. In some embodiments of compounds of general formula (B), b is 3 for the ring containing G, and b is 0 for the other ring. In some embodiments, when b is 3, two of the substituents join to form a fused aryl ring.

In some embodiments, a compound of general formula (B) has the structure of general formula (D) as shown below:

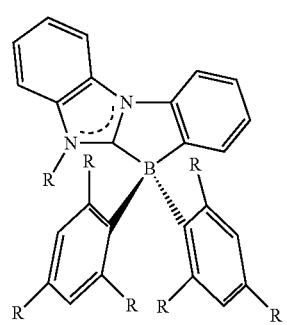

(D)

wherein R is hydrogen (H), alkyl, aryl, or BAr$_2$. In an embodiment, R is methyl and the compound is compound 15:

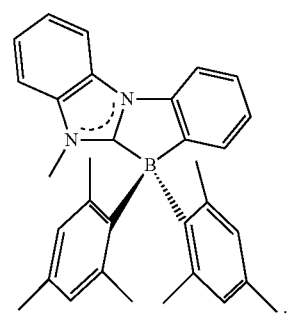

15

In some embodiments, a compound of general formula (B) has the structure of general formula (E) as shown below:

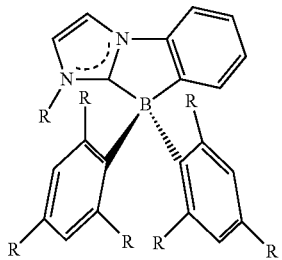

(E)

wherein R is hydrogen (H), alkyl, aryl, or BAr$_2$. In an embodiment, R is methyl and the compound is compound 16:

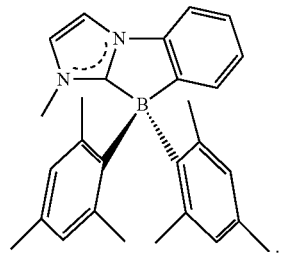

16

In an embodiment, organoboron compounds have the structure of general formula (C) as shown below:

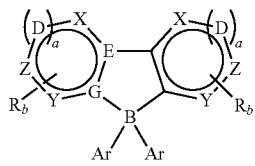

(C)

wherein
B is boron;
G is nitrogen, sulfur, substituted or unsubstituted carbon, or oxygen;
D is substituted or unsubstituted nitrogen, sulfur, substituted or unsubstituted carbon, or oxygen;
a is zero or one;
X, Y and Z are independently oxygen, sulfur, substituted or unsubstituted nitrogen, or substituted or unsubstituted carbon;
E is substituted or unsubstituted nitrogen, or substituted or unsubstituted carbon;
Ar is independently a substituted or unsubstituted aryl moiety wherein at least one of the two Ar moieties is bi-, tri-, tetra-, or penta-substituted aromatic moiety that has substitutents located at least in the two ortho positions relative to the boron-Ar bond, and optionally there are substituents located in the meta and/or para positions as well;
R is a substituent; and
b is a number from 0 to 5;
wherein substituents include aliphatic groups, alkoxyl, silyl, siloxyl, aryl, B(aliphatic)(aryl), B(aryl)$_2$, or any combination thereof, wherein a substituent may be further substituted, and wherein two substituents can join to form a fused aryl ring.

In some embodiments, compounds of general formula (C) are photochromic.

In an embodiment, organoboron compounds have the structure of general formula (C) as shown below:

In some embodiments of compounds of general formula (C), G is carbon. In some embodiments, E is nitrogen. In some embodiments, G is carbon and E is nitrogen.

In some embodiments of compounds of general formula (C), G is carbon, E is nitrogen, Y in the ring containing G is nitrogen, and Y in the other ring is carbon.

In some embodiments of compounds of general formula (C), a is 0. In some embodiments of compounds of general formula (C), a is 1 in the ring containing G, and a is 0 in the other ring.

In some embodiments of compounds of general formula (C), Ar is 1,3,5-mesityl.

In some embodiments of compounds of general formula (C), b is 1 for the ring containing G, and b is 0 for the other ring. In some embodiments of compounds of general formula (C), b is 3 for the ring containing G, and b is 0 for the other ring. In some embodiments, when b is 3, two of the substituents join to form a fused aryl ring.

In some embodiments of compounds of general formula (C), X is carbon, and at least one of Z, D and Y is a heteroatom.

In certain embodiments of compounds of general formula (C), one of X, Y, D and Z is nitrogen, another one of X, Y, D and Z is sulfur or oxygen, and at least one of X, Y, D and Z is carbon. In some embodiments of general formula (C), X is oxygen or sulfur, and both Y and Z are carbon. In some embodiments of general formula (C), one of X, Y and Z is nitrogen, and the remaining two of X, Y and Z are carbon. In some embodiments, two of X, Y and Z are nitrogen, and the remaining one of X, Y and Z is carbon. In some embodiments of general formula (C), all three of X, Y and Z are nitrogen.

In some embodiments of compounds of general formula (C), a is one in both instances, G is nitrogen, X, Y, and Z are carbon, one b is zero and the other b is not zero.

In some embodiments, when a is one in both instances, and for the ring that includes G, G is nitrogen, b is one, and R is —B(Mes)$_2$, —C≡C-phenyl, —CH(═O), or —C≡C-phenyl; then the other b is not zero.

In some embodiments of compounds of general formula (C), a is 1 in both instances and for the ring that includes G, b is one and R is B(Mes)$_2$; then the other b is not zero.

In some embodiments of compounds of general formula (C), a is 1 for the ring that includes G and 0 for the other ring, and G is carbon.

In some embodiments of compounds of general formula (C), a is zero for the ring that contains E and is one for the other ring; one of the Y atoms (the one in the ring with the E atom) is substituted nitrogen such as, for example, N—CH$_3$; the other Y is carbon; E is nitrogen; G is carbon; Z and X are carbon; for the ring that contains E, b is 1, R$_1$ is CH$_3$ on Y, and the valences are filled by hydrogen for Z and X; for the other ring, D is carbon, b is 4, and R$_1$, R$_2$, R$_3$, and R$_4$ on Y, Z, D and X, respectively, are the same, or, for the other ring, D is carbon and b is 0.

In some embodiments of compounds of general formula (C), a is zero for the ring that contains E and is one for the other ring; one of the Y atoms (the one in the ring with the E atom) is substituted nitrogen such as, for example, N—CH$_3$; the other Y is carbon; E is nitrogen; G is carbon; Z and X are carbon; for the ring that contains E, b is 1, R$_1$ is CH$_3$ on Y, and the valences are filled by hydrogen for Z and X; for the other ring, D is carbon, b is 2, and the two R groups join to form a fused aromatic group such as, for example, a benzene ring with Y and Z, D and Z, or X and D.

In some embodiments of compounds of general formula (C), a is zero for the ring that contains E and is one for the other ring; one of the Y atoms (the one in the ring with the E atom) is substituted nitrogen such as N—CH₃; the other Y is carbon; E is nitrogen; G is carbon; Z and X are carbon; for the ring that contains E, b is 3, R₁ is CH₃ on Y, and R₂ and R₃ join to form a fused aromatic ring such as, for example, a benzene ring along with Z and X; for the other ring, D is carbon, b is 4, and R₁, R₂, R₃ and R₄ on Y, Z, D and X, respectively, are the same, or, for the other ring, D is carbon and b is 0.

In some embodiments of compounds of general formula (C), a is zero for the ring that contains E and is one for the other ring; one of the Y atoms (the one in the same ring with the E atom) is substituted nitrogen such as, for example, N—CH₃; the other Y is carbon; E is nitrogen; G is carbon; Z and X are carbon; for the ring that contains E, b is 3, R₁ is CH₃ on Y, and R₂ and R₃ join to form a fused aromatic ring such as, for example, a benzene ring along with Z and X; for the other ring, D is carbon, b is 2, and the two R groups join to form a fused aromatic group such as, for example, a benzene ring with Y and Z, D and Z, or X and D.

Embodiments of photochromic organoboron compounds provided herein are suitable for use in photochromic and sensing applications for several reasons: (i) they can be quantitatively switched between two isomers; (ii) dramatic color changes can be achieved even at low conversion; (iii) photoisomerization is accompanied by reversible fluorescence quenching; (iv) photoisomerization rates and quantum efficiencies are high; and (v) fluorescence color and absorption color are highly tunable. Photochromic organoboron compounds described herein are promising for applications such as, for example, molecular switches, optical memory devices, optical data storage, electronic paper, oxygen sensors, ophthalmic glasses, smart windows, UV blocking materials, and combinations thereof. Synthetic details and characterization data for representative examples of this class of photochromic compounds are presented herein. In addition, experimental data demonstrating the use of the new materials for oxygen sensing, photochromic switching and UV-blocking in polymer matrices is also provided.

Embodiments of compounds described herein are photochromic and so they switch between two color states. The switching is caused by a reversible structural transformation around a tetrahedral boron centre that leads to a distinct color change between a transparent light-colored state and a translucent, dark-colored state. As a result, the organoboron materials are highly tunable in terms of color in both the light-colored state (fluorescence) and the dark-colored state (absorbance), as well as in terms of stability and switchablility. Changes in structure, such as changing one substituent group, may greatly affect the color of the molecule, for example from dark blue to dark green in the dark state. Organoboron compounds described herein are highly fluorescent in the light-colored or colorless state and are non-fluorescent in the dark-colored state. This changing characteristic provides an additional and convenient way to monitor a switching event. Embodiments of the invention provide a molecular switch using compounds of general formula (A), (B), (C), (D) or (E).

Embodiments of compounds of general formula (A), (B), (C), (D) or (E) are strong UV light absorbers. Certain embodiments are capable of blocking UV light and are useful for technologies wherein protection from UV penetration is desirable. For example, it may be desirable to protect art, furniture, food, and the from UV light. Protective barriers using embodiments of the invention can provide such a UV barrier. In certain embodiments it is useful for a colour change to occur when the barrier is exposed to UV light. In other embodiments, it is desirable if little to no colour change is apparent when the UV protection is activated.

Embodiments of compounds of general formula (A), (B), (C), (D) or (E) are controlled by light, i.e., transformed from a non-reactive state to a reactive state when irradiated by light. This stepwise transformation controlled by light is useful in, e.g., light-controlled chemical reactions and transformation.

Certain embodiments of the invention provide methods of making compounds of general formula (A), (B), (C), (D) or (E). The following reaction schemes are provided as an overview to synthetic procedures that are outlined in detail in the Working Examples. In Scheme 1, a general synthetic procedure for compounds of general formula (A) is provided, using a structural embodiment as an example. In the second reaction scheme, a synthetic scheme is presented for certain compounds of general formula (A) that are used as representative examples in several studies described in the Working Examples.

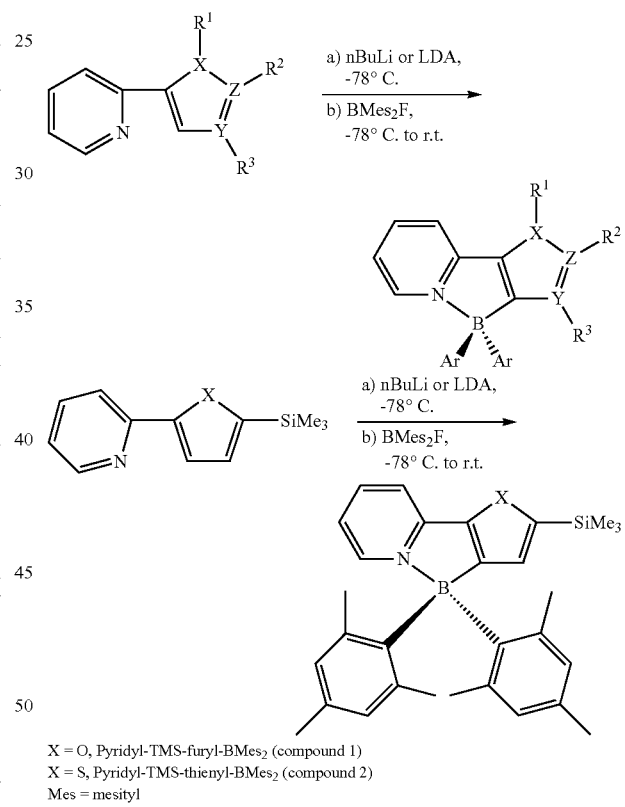

X = O, Pyridyl-TMS-furyl-BMes₂ (compound 1)
X = S, Pyridyl-TMS-thienyl-BMes₂ (compound 2)
Mes = mesityl In certain embodiments, the invention provides methods of making a composition comprising compounds of general formula (A), (B), (C), (D) or (E) and polymer. Techniques include adding the boron compounds to a polymer matrix, adding the boron compounds to a mixture that polymerizes to form a polymer, or forming a chemical bond between the compounds and a component of the polymer or monomer either before or after polymerization. In the non-limiting examples provided herein, the boron compounds are added into the polymer matrix (doped).

Examples of polymers suitable for mixing with organoboron compounds include homopolymers and co-polymers.

Non-limiting examples include poly(dimethylsiloxane) ("PDMS"), polystyrene (PS), polyethylene (PE), polyvinylcarbazole (PVK), poly(methyl methacrylate) ("PMMA"), copolymers of polyethylene-co-vinyl alcohol) ("EVOH"). It may be possible to crosslink to other polymers such as EVOH, to improve properties (e.g., oxygen stability, isomerization rate) before or after mixing with photochromic compounds. Hybrid materials such as polymeric matrices that are doped with photochromic compounds can be used, for example, as films. Such hybrid materials provide inexpensive UV-blocking or color-switching devices. Most previously known photochromic compounds included metal atoms and provided expensive products with limited color range and contrast. As described in the Working Examples, as shown in the drawings, certain compounds of general formula (A), (B), (C), (D) or (E) have demonstrated superior qualities as UV-blocking and/or color-switching. FIGS. 5A-8B clearly show the ability of representative compositions comprising polymer matrices PS and PMMA doped with various amounts of representative compounds 1 and 2, to change color upon exposure to light.

EVOH is a excellent polymer candidate for UV-blocking applications such as food packaging, and in photochromic eyeglasses. Although not wishing to be bound by theory, the inventors suggest that these color disappearances are due to the formation of deborylated C—C coupled product. Most importantly, the dark colored isomer also reacts with oxygen in a polymer matrix (PS, PDMS), changing color from dark blue or dark purple to colorless. PDMS and PS were chosen as substrates for oxygen sensing because both are widely used in the literature as substrates for sensing oxygen with moderate or high permeability for oxygen (Lee, S. K.; Okura, I., *Analytical Communications*, (1997) 34, 185; Cox, M. E. *J. Polym. Sci.: Part A: Polym Chem.* (1986) 24, 621).

In certain embodiments, bulky substituents that offer steric effects are covalently bonded to the photochromic organoboron compounds. Such bulky groups enhance the switching rates and the stability of the compounds, as well as enhancing their compatibility with a surrounding polymer matrix. Certain substituents can enhance solubility properties in a polymer matrix.

Previously known photochromic compounds such as DTE (diarylethyene, e.g., dithienylethene) possess a photostationary state. As a result, it is often not possible to fully switch such a compound from its colorless state to its dark-colored state. Also, DTE is sensitive to visible light, and its dark state is unstable in ambient light. In contrast, certain photochromic organoboron compounds described herein do not have a photostationary state. Thus it is possible to achieve 100% conversion to the dark-colored state using light (usually UV light). Also in contrast, certain photochromic organoboron compounds of general formula (A), (B), (C), (D) or (E) do not switch back from dark-colored to transparent by exposure to visible light. Certain of the organoboron compounds described herein are able to switch back from dark to transparent by exposure to thermal energy.

An advantageous property of embodiments of the organoboron compounds described herein is that the dark isomers are highly sensitive toward oxygen. Upon exposure to oxygen, the dark isomer loses its color and becomes colorless or light yellow rapidly in either solution or solid state. Thus, this class of compounds has potential for use as switchable oxygen sensing materials. Accordingly, such compounds are suitable for use as oxygen indicators, oxygen detectors, and/or oxygen sensors. Effective oxygen indicators are useful in, for example, chemical, biochemical, and/or medicinal applications. For example, an oxygen indicator associated with packaging of an oxygen-sensitive chemical could indicate whether the chemical had become exposed to oxygen, and an oxygen indicator disposed on food packaging could indicate to a manufacturer or retailer which food packages have become exposed to oxygen (e.g., improperly sealed, packaged food has degraded).

Most of the previously known photochromic compound, such as DTE, do not show high sensitivity to oxygen. In contrast, embodiments of organoboron compounds described herein show a high sensitivity toward oxygen in their dark-colored state. Such compounds are suitable as oxygen indicators. In oxygen sensing situations it may be appropriate to embed the compound(s) in suitable oxygen-permeable polymer matrices (e.g., PDMS).

Compositions comprising a compound of general formula (A), (B), (C), (D) or (E) and a polymer may be applied to a substrate. Non-limiting examples of such substrates include glass, plastic, and paper. Techniques for causing isomerization in these compositions (either when applied to a substrate or alone) include exposure to light, which may be natural sunlight, artificial light, a UV source such as a UV light, a UV gun, or a UV pen.

Figure 1B:
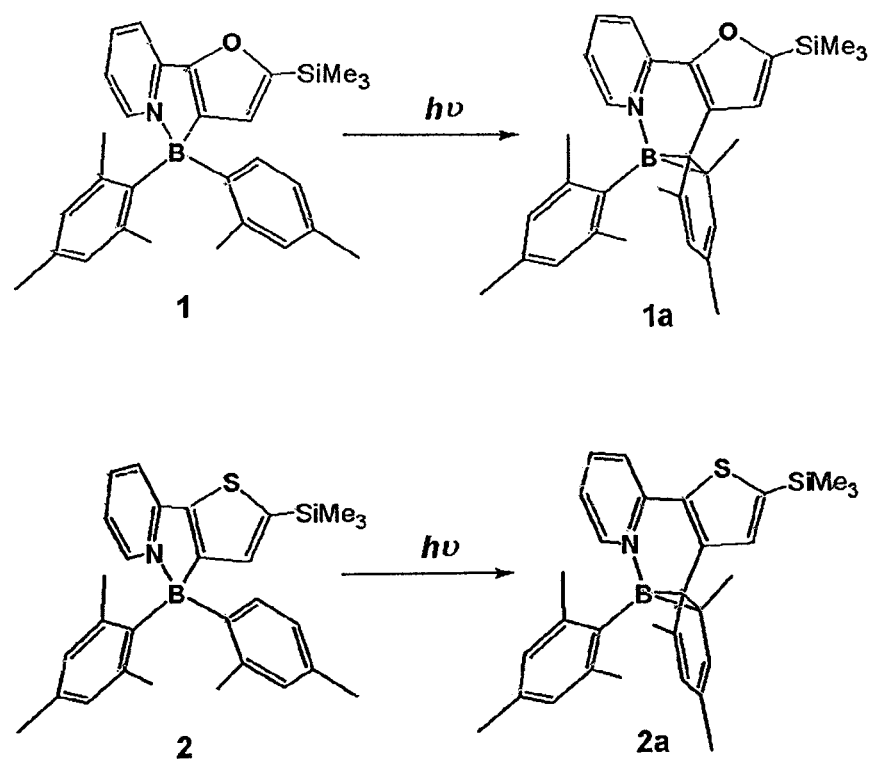
FIG. 1B shows structural formulae for isomerization of the compounds of FIG. 1A when they were exposed to light, using representative example compounds 1 converting to 1a and 2 converting to 2a for conditions such as exposure to light (represented as hv).
Figure 2A:
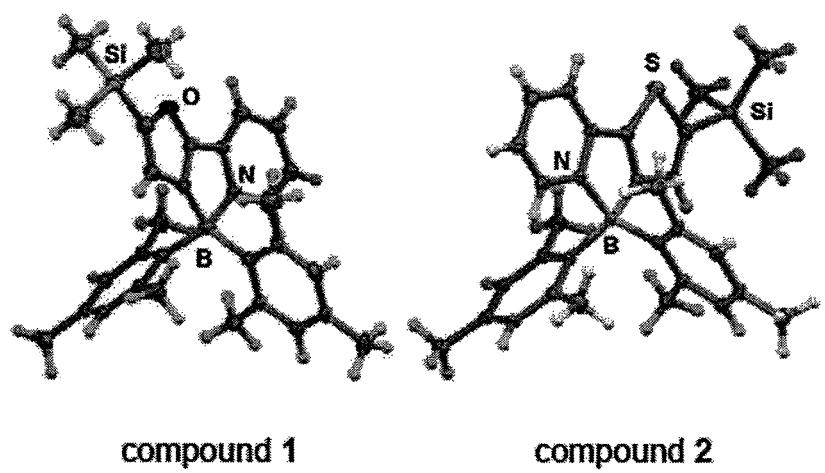
FIG. 2A shows X-ray crystallographic structures for compound 1 (left) and compound 2 (right) determined by single-crystal X-ray diffraction analysis with 35% thermal ellipsoids.
Figure 2B:
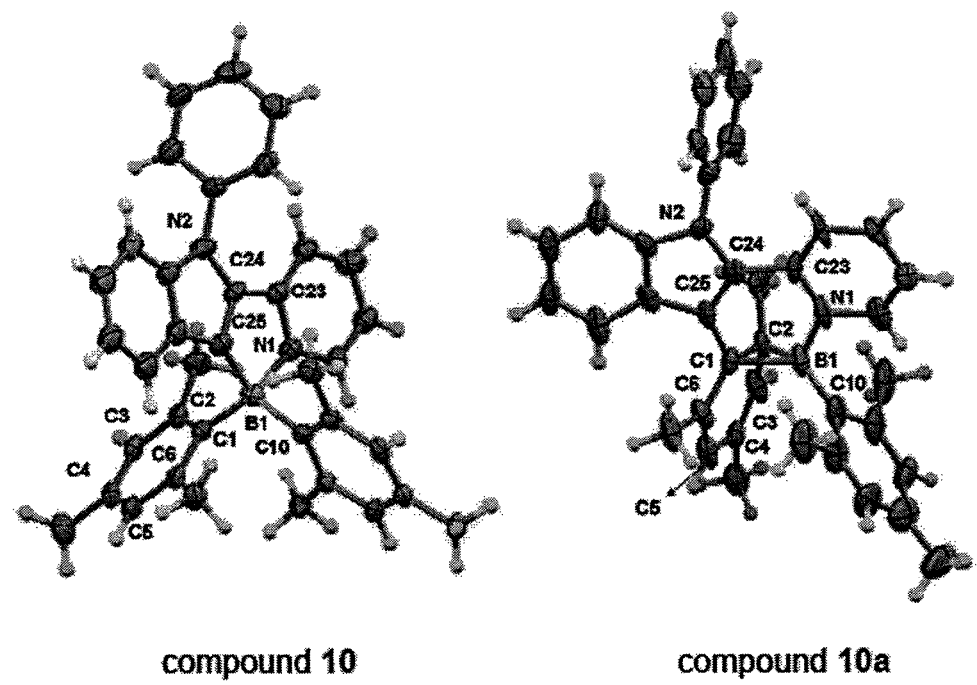
FIG. 2B shows X-ray crystallographic structures for compounds 10 and its dark-colored isomer compound 10a determined by single-crystal X-ray diffraction analysis.
Figure 2C:
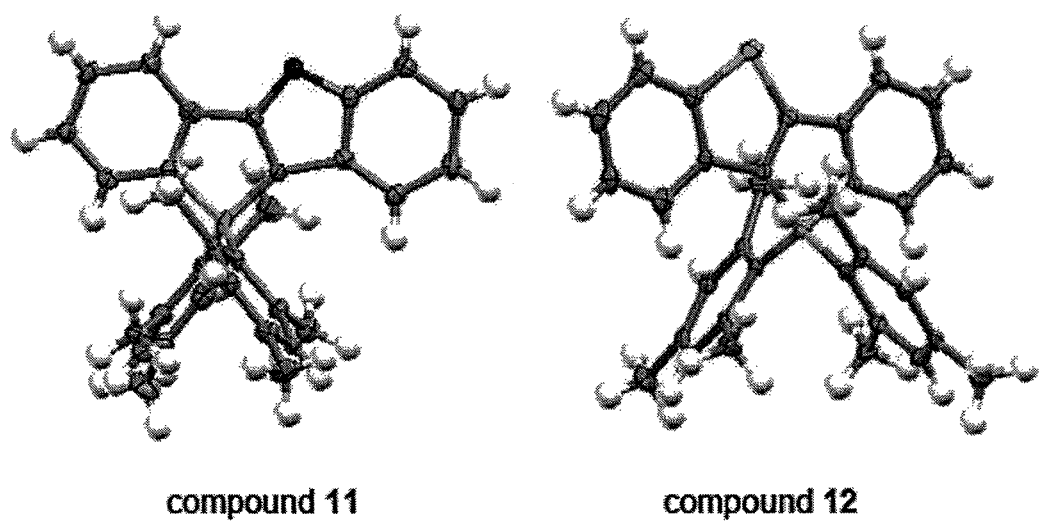
FIG. 2C shows X-ray crystallographic structures for compounds 11 (left) and 12 (right) determined by single-crystal X-ray diffraction analysis.
Figure 2D:
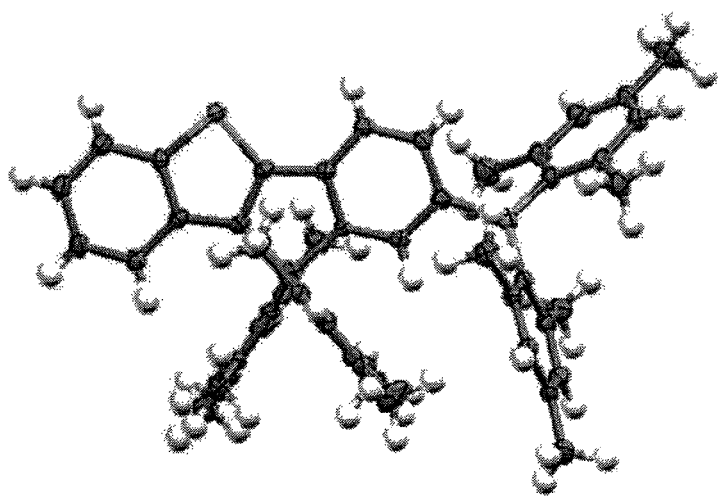
FIG. 2D shows X-ray crystallographic structures for compound 14 determined by single-crystal X-ray diffraction analysis.

Referring to FIGS. 1A and 1B, in FIG. 1A structural formulae are shown for compounds of general formula (A), while in FIG. 1B, structural formulae are shown for isomerization of the compounds of FIG. 1A when they were exposed to light, using representative example compounds 1 converting to 1a and 2 converting to 2a for conditions such as exposure to light (represented as hv).

Referring to FIGS. 2A-D shows X-ray crystallographic structures for compound 1, compound 2, compound 10, its dark-colored isomer compound 10a, compound 11, compound 12, and compound 14.

Figure 3:
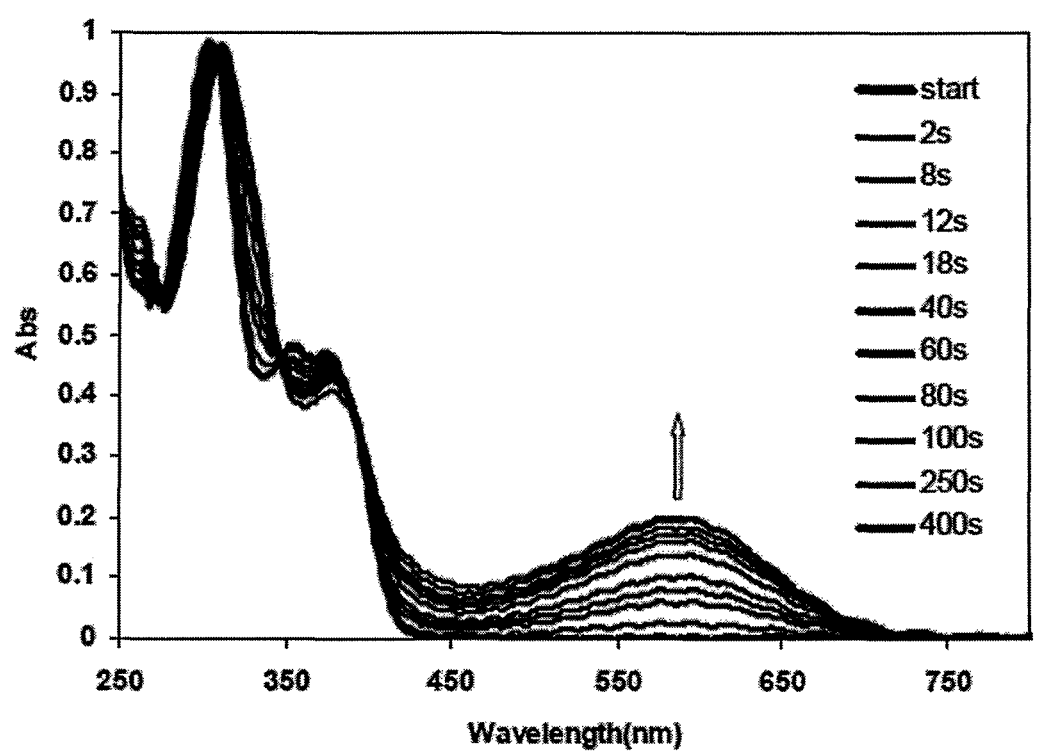
FIG. 3 is a plot of absorbance versus wavelength and shows the absorption spectral change of compound 2 in a polystyrene (PS) film upon irradiation at 365 nm; the photoisomerization was completed in approximately 400 seconds.

Referring to FIG. 3, a plot is shown of absorbance versus wavelength and shows the absorption spectral change of compound 2 in a PS film upon irradiation at 365 nm; the photoisomerization was completed in approximately 400 seconds.

Figure 4:
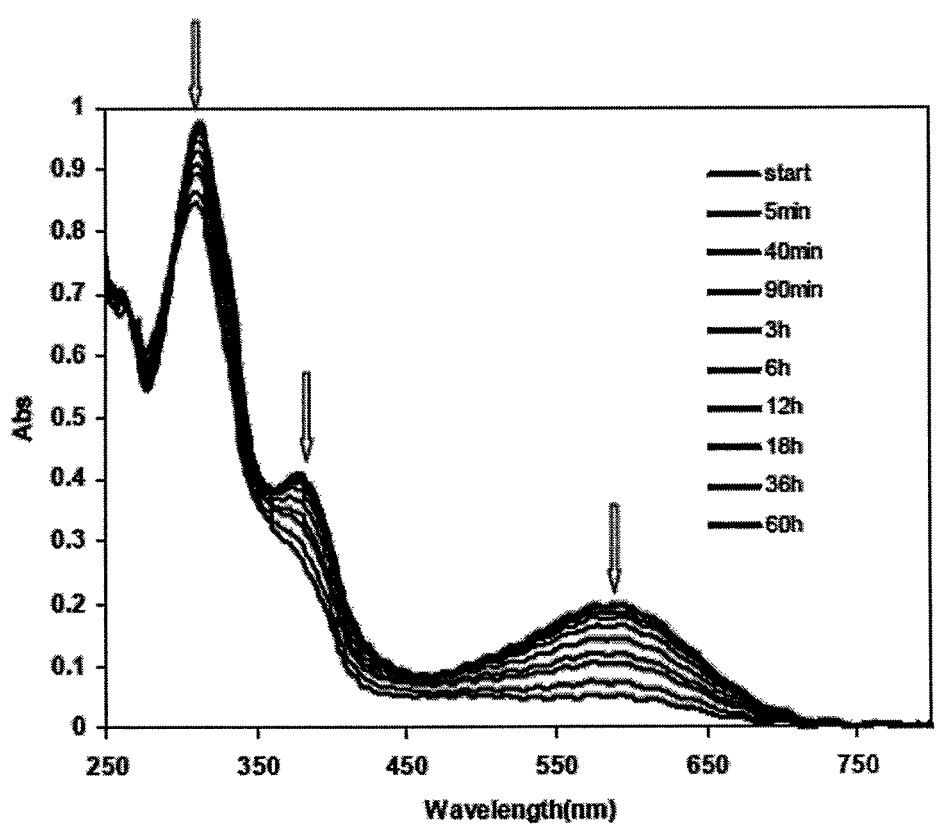
FIG. 4 is a plot of absorbance versus wavelength and shows the UV-vis spectral change of the dark-colored isomer of compound 2 in a PS film upon exposure to oxygen; the peak at 590 nm had disappeared completely after about two days.

Referring to FIG. 4, a plot is shown of absorbance versus wavelength and shows the UV-vis spectral change of the dark-colored isomer of compound 2 in a PS film upon exposure to oxygen; the peak at 590 nm had disappeared completely after about two days.

Referring to FIGS. 5A and 5B, a plot is shown of absorbance versus wavelength and shows the absorption spectra for PS films doped by specified amounts of compound 1, while FIG. 5B shows absorbance versus mass of compound 1 in 200 mg PS and shows a linear dependence of the absorbance at 350 nm with the amount of compound 1 in PS.

Referring to FIGS. 6A and 6B, a plot is shown of absorbance versus wavelength and shows the absorption spectra for PMMA films doped by specified amounts of compound 1, while FIG. 6B shows absorbance versus mass of compound 1 in 200 mg PMMA and shows a linear dependence of the absorbance at 350 nm with the amount of compound 1 doped in PMMA.

Referring to FIGS. 7A and 7B, in FIG. 7A a plot is shown of absorbance versus wavelength and shows the absorption spectra for PS films doped by specified amounts of compound 2, while in FIG. 7B a plot is shown of absorbance versus mass of compound 2 in 200 mg PS and shows a linear dependence of the absorbance at 350 nm with the amount of compound 2 doped in PS.

Referring to FIGS. 8A and 8B, in FIG. 8A a plot is shown of absorbance versus wavelength and shows the absorption spectra for PMMA films doped by specified amounts of compound 2, while in FIG. 8B, a plot is shown of absorbance versus mass of compound 2 in 200 mg PMMA and shows a linear dependence of the absorbance at 350 nm with the amount of compound 2 in PMMA.

Figure 9:
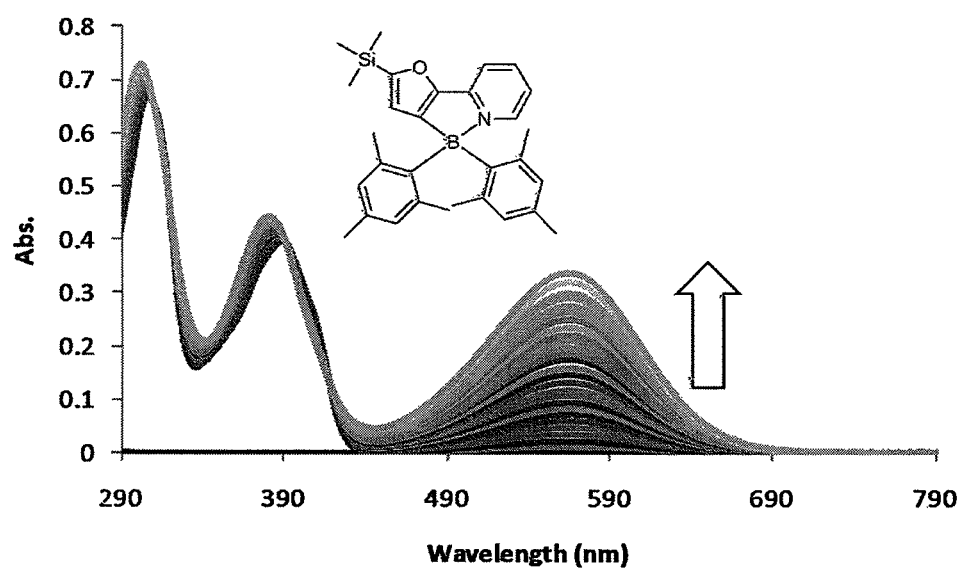
FIG. 9 is a plot of absorbance versus wavelength to indicate the UV-vis spectral changes recorded at 2 second intervals for compound 1 in toluene upon exposure to UV light (365 nm).

Referring to FIG. 9, a plot is shown of absorbance versus wavelength to indicate the UV-vis spectral changes recorded at 2 second intervals for compound 1 in toluene upon exposure to UV light.

Figure 10:
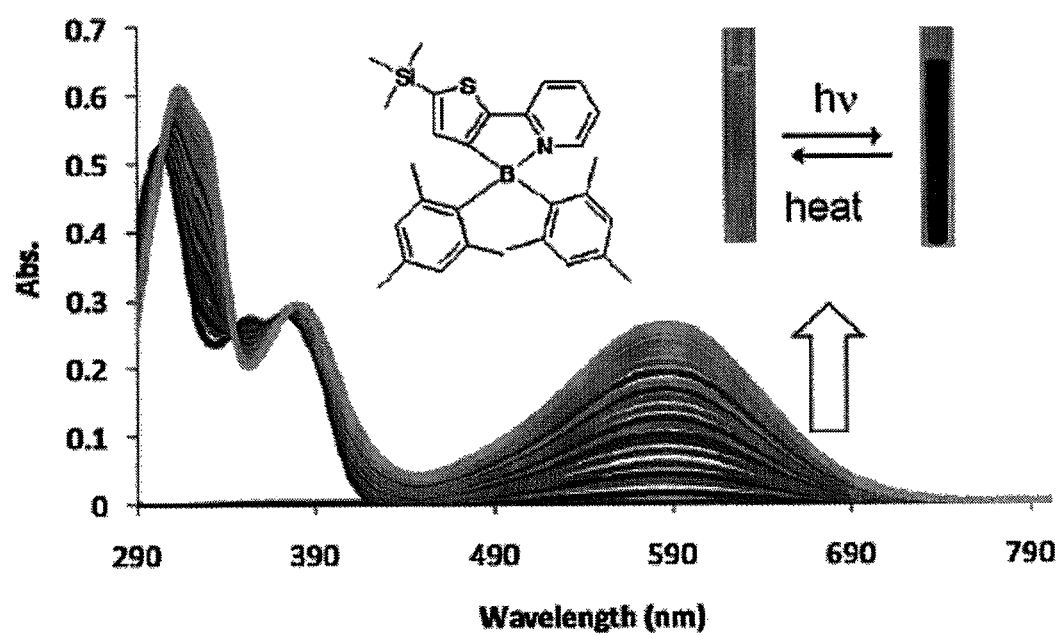
FIG. 10 is a plot of absorbance versus wavelength to indicate the UV-vis spectral changes recorded at 1 second intervals for compound 2 in toluene upon exposure to UV light (365 nm). An insert at the top right is a photograph showing the color change seen in the solution.

Referring to FIG. 10, a plot is shown of absorbance versus wavelength to indicate the UV-vis spectral changes recorded at 1 second intervals for compound 2 in toluene upon exposure to UV light. An insert at the top right is a photograph showing the color change from colorless to dark-colored seen in the solution upon exposure to light (represented as hv) and the color change from dark-colored to colorless seen in the solution upon exposure to heat.

Figure 11:
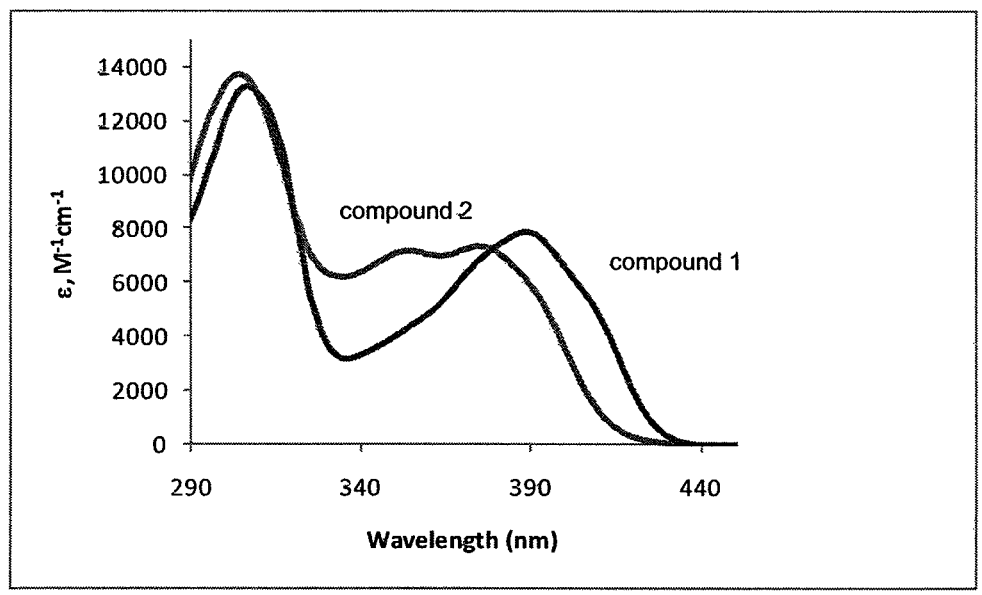
FIG. 11 is a plot of molar absorptivity coefficient versus wavelength to show intensity in the near UV region for compounds 1 and 2 in toluene ($10^{-5}$ M).

Referring to FIG. 11, a plot is shown of molar absorptivity coefficient versus wavelength to show intensity in the near UV region for compounds 1 and 2 in toluene ($10^{-5}$ M).

Figure 12:
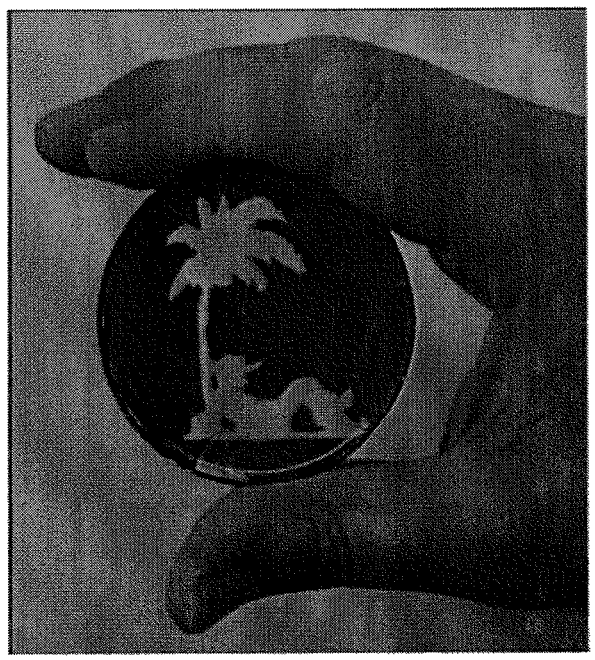
FIG. 12 is a photograph showing use of photochromic compound 2 (about 5 mg in 2.5 g polymer) for patterning. The compound was doped in polystyrene polymer matrix wherein a dark area was produced by exposing an area to UV (365 nm) irradiation while the colourless area was blocked from UV using a patterned mask.

Referring to FIG. 12, a photograph is shown to demonstrate use of photochromic compound 2 for patterning. A composition was prepared by adding compound 2 to a polystyrene (PS) polymer matrix. Following preparation, a dark area was produced by exposing an area to UV irradiation while a patterned colourless area was blocked from UV using a patterned mask. The result is a patterned product. This technique could be used to produce a variety of dark on light background, or light on dark background products. Such products may include text (e.g., electronic paper). Advantageously, such a product could be regenerated into a wholly colourless or a wholly dark-coloured product by exposure to the appropriate isomerizing trigger as described herein (e.g., heat, UV light, light of a different energy, oxygen).

WORKING EXAMPLES

All experiments were carried out under an atmosphere of nitrogen using standard Schlenk techniques or in a dry box. THF and toluene were purified using a solvent purification system (available from Innovation Technology, Inc.). $C_6D_6$ was dried over $CaH_2$. $^1H$, $^{13}C$, and $^{11}B$ NMR spectra were recorded on a Bruker Avance 400 or 500 MHz spectrometer (Bruker, East Milton, Ontario, Canada). Fluorescence spectra were recorded on a Photon Technologies International QuantaMaster Model C-60 spectrometer (Birmingham, N.J., USA). UV-Vis spectra were recorded on a Cary 50 spectrometer (available from Varian, Inc., Palo Alto, Calif., USA). High resolution mass spectra (HRMS) were obtained using a Waters/Micromass GC-TOF spectrometer (electron ionization "EI" mode) (Waters, Milford, Mass., USA). 2-(2-thienyl)pyridine was purchased from Aldrich (Oakville, ON, Canada). 2-(2-furyl)pyridine was made using a modified literature procedure (Molander, G. A.; Canturk, B.; Kennedy, L. E. J. Org. Chem. 2009, 74, 973). 2-(5-(trimethylsilyl)furan-2-yl)pyridine and 2-(5-(trimethylsilyl)thiophen-2-yl)pyridine were prepared using a modified literature procedure (Ribereau, P.; Queguiner, G. Tetrahedron. 1983, 21, 3593).

Example 1

Fluorescence Quantum Yield Measurements

Fluorescence quantum yields were measured in dilute degassed toluene solution (Abs.=~0.1) at room temperature using the relative quantum yield method using 9,10-diphenylanthracene as the reference standard (Φ=0.90) (Demas, N. J.; Crosby, G. A. J. Am. Chem. Soc. 1970, 92, 7262; Fery-Forgues, S.; Lavabre, D. J. Chem. Ed. 1999, 9, 1260.) Data are presented in Table 1.

Example 2

Monitoring Photolysis Process Via $^1H$ NMR Spectra

Samples were dissolved in dry $C_6D_6$ in an NMR tube under $N_2$ (~0.5 mg in 0.5 mL solvent). To remove any traces of oxygen that might be present in the NMR tube, 2 freeze-thaw cycles were performed using liquid $N_2$. Photolysis was then performed using a UV reactor (350 nm) at room temperature, followed by recording $^1H$ NMR spectra after an exposure time. Photochromic conversion in the solution state was thus confirmed both by $^1H$ NMR and UV-vis absorption spectra for compounds 1, 2, 8, 9, 10, 11, 12, 13 and 14.

Example 3

General Procedure for Monitoring Photolysis Via UV-Vis Spectroscopy

Samples were dissolved in dry degassed toluene in a quartz cuvette (~$10^{-5}$ M) with a screw cap, under an inert atmosphere in a dry box. Photolysis was performed using a handheld UV lamp (365 nm) at room temperature. UV-vis spectra were recorded after certain exposure time (5-20 s). Data are presented in Table 1.

Example 4

General Procedure for the Measurement of Photoisomerization Quantum Yields

Quantum yields of photoisomerization of all compounds were determined using ferrioxalate actinometry. An Ocean Optics fibre optic spectrophotometer (Ocean Optics, Dunedin, Fla., USA) connected to a four-way temperature-controlled cuvette holder (available from Quantum Northwest, Liberty Lake, Wash., USA) via 400 μm optical fibers was used to measure the absorbance with an irradiation source (200 W Hg/Xe lamp) attached to a monochromator (available from Photon Technology International, Edmonton, Alberta, Canada). Measurements were conducted four times for each compound, including the reference compound. A typical concentration used for the boryl compounds is ~$6.0 \times 10^{-5}$ M in toluene. Quantum Efficiency (or quantum yield) obtained was the average value of four measurements with an uncertainty about ±0.03 to 0.05.

Example 5

Synthesis and Characterization

Syntheses of photochromic organoboron compounds was readily achieved by lithiating the appropriate chelate ligand in a toluene solution by using either n-butyl lithium or LDA (lithium di(isopropyl)amide) at −78° C., followed by the addition of $BAr_2X$ (where Ar=aryl, X=halide such as fluoride or chloride), followed by gradual warming of the solution to room temperature (r.t.). Chelate ligands used in the above syntheses were prepared by modified literature methods. First, Suzuki-Miyaura cross coupling reaction between 2-bromopyridine and the corresponding boronic acid of thiophene or furan was performed, which was followed by lithiation at the 2-position of the furan or thiophene ring, and addition of trimethylsilylchloride. Detailed synthetic procedures and characterization data for compounds Pyridyl-TMS-Furyl-$BMes_2$ (compound 1) and Pyridyl-TMS-Thienyl-$BMes_2$ (compound 2) are provided in Examples 5A and 5B.

Example 5A

Synthesis of pyridyl-TMS-Furyl-BMes2 (Compound 1)

To a solution of 2-(5-(trimethylsilyl)furan-2-yl)pyridine (0.3 g, 1.38 mmol) in THF (40 mL), at −78° C., n-BuLi (1.6 M in hexane, 0.88 mL, 1.4 mmol) was added slowly and mixed for 60 min while maintaining temperature at −78° C. Then, a THF solution (30 mL) of BMes$_2$F (0.42 g, 1.4 mmol) was added slowly via cannula and the resulting mixture was stirred overnight. Solvent was removed under reduced pressure and a resulting solid was dissolved in CH$_2$Cl$_2$ and quenched with 10 mL H$_2$O. An aqueous liquid layer and a hydrophobic liquid layer resulted. The hydrophobic layer was separated, dried over MgSO$_4$, and filtered. CH$_2$Cl$_2$ solvent was removed under reduced pressure. A residue was purified by flash column chromatography over silica gel using CH$_2$Cl$_2$/hexanes mixture (1:4) to give a yellow powder. The powder was recrystallized from CH$_2$Cl$_2$/hexanes to give yellow crystals (0.31 g, 48%). HREI-MS (high resolution mass spectrum in electron ionization mode) (M)$^+$: Anal. Calcd for C$_{30}$H$_{36}$BNOSi, 465.2659. found: 465.2672. $^1$H NMR (CD$_2$Cl$_2$): δ 8.41 (d, 1H, $^3$J=4.8), 7.91 (t, 1H, $^3$J=7.6), 7.60 (d, 1H, $^3$J=8.0), 7.02 (t, 1H, $^3$J=6.6), 6.82 (s, 1H), 6.65 (s, 4H), 2.19 (s, 6H), 1.84 (s, 12H), 0.33 (s, 9H). $^{13}$C NMR (CD$_2$Cl$_2$): δ 168.4, 155.2, 149.4, 147.4, 141.4, 140.6, 134.2, 129.8, 123.9, 118.6, 115.0, 24.3, 20.7, −1.6. $^{11}$B NMR (CD$_2$Cl$_2$): δ 6.44.

Example 5B

Synthesis of pyridyl-TMS-Thienyl-BMes$_2$ (Compound 2)

To a solution of 2-(5-(trimethylsilyl)furan-2-yl)pyridine (1.4 g, 6.0 mmol) in THF (50 mL), at −78° C., n-BuLi (1.6 M in hexane, 6.0 mL, 3.8 mmol) was added slowly and mixed for 60 min at −78° C. Then, a THF solution (40 mL) of BMes$_2$F (1.8 g, 6.0 mmol) was added slowly via cannula and the resulting mixture was stirred overnight. Solvent was removed under reduced pressure and a resulting solid was dissolved in CH$_2$Cl$_2$ and quenched with 10 mL H$_2$O. An aqueous liquid layer and a hydrophobic liquid layer resulted. The hydrophobic layer was separated and dried over MgSO$_4$ and filtered. CH$_2$Cl$_2$ was removed under reduced pressure. A residue was purified by flash column chromatography over silica gel using CH$_2$Cl$_2$/hexanes mixture (1:4) to give a yellow powder. The powder was recrystallized from CH$_2$Cl$_2$/hexanes to give yellow crystals (1.35 g, 47%). HREI-MS (M)$^+$: Anal. Calcd for C$_{30}$H$_{36}$BNSSi, 481.2431. found: 481.2445. $^1$H NMR (CD$_2$Cl$_2$): δ 8.47 (d, 1H, $^3$J=6.0), 7.92 (t, 1H, $^3$J=7.5), 7.62 (d, 1H, $^3$J=8.0), 7.41 (s, 1H), 7.10 (t, 1H, $^3$J=6.5), 6.69 (s, 4H), 2.25 (s, 6H), 1.85 (s, 12H), 0.39 (s, 9H). $^{13}$C NMR (CD$_2$Cl$_2$): δ 155.3, 149.9, 146.7, 141.2, 140.5, 139.2, 136.8, 134.2, 129.9, 119.3, 117.6, 24.4, 20.7, −0.04. $^{11}$B NMR (CD$_2$Cl$_2$): δ 6.51.

Example 5C

Synthesis of BnzFuPyB (Compound 8)

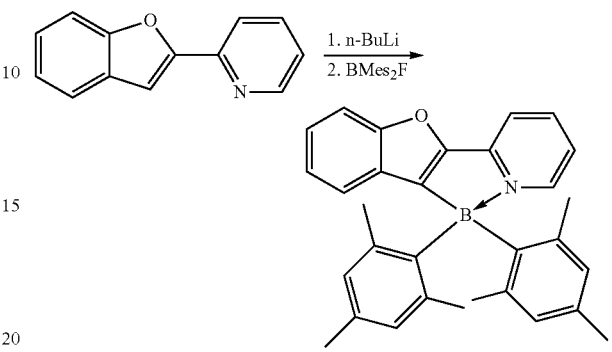

To a solution of 2-(Benzofuran-2-yl)pyridine (0.4 g, 2.0 mmol) in THF (50 mL), at −78° C., n-BuLi (1.6 M in hexane, 1.25 mL, 2.0 mmol) was added slowly and mixed for 60 min at −78° C. Then, a THF solution (30 mL) of BMes$_2$F (0.6 g, 2.0 mmol) was added slowly using a cannula and stirred overnight. Solvents were removed under reduced pressure and the resulting solid was dissolved in CH$_2$Cl$_2$ and quenched with 10 mL H$_2$O. The organic layer was separated and dried over MgSO$_4$ and filtered. After CH$_2$Cl$_2$ was removed under reduced pressure, the residue was purified over silica gel by flash column chromatography using CH$_2$Cl$_2$/hexanes mixture (1:4) to give a yellow powder, which was recrystallized from CH$_2$Cl$_2$/hexanes to give yellow crystals (0.58 g, 66%). HREI-MS (M)$^+$: Anal. Calcd for C$_{31}$H$_{30}$BNO, 443.2420. Found: 443.2436. $^1$H NMR (CD$_2$Cl$_2$): δ 8.57 (d, 1H, $^3$J=5.6), 8.00 (t, 1H, $^3$J=7.7), 7.79-7.77 (m, 2H), 7.56 (d, 1H, $^3$J=8.4), 7.35 (t, 1H, $^3$J=7.6), 7.24-7.15 (m, 2H), 6.68 (s, 4H), 2.19 (s, 6H), 1.92 (s, 12H). $^{13}$C NMR (CD$_2$Cl$_2$): δ 160.2, 151.9, 149.9, 147.3, 141.3, 140.1, 134.5, 130.3, 130.1, 126.2, 124.2, 123.5, 120.1, 116.2, 112.2, 24.7, 20.7. $^{11}$B NMR (CD$_2$Cl$_2$): δ 7.93

Example 5D

Synthesis of (benzothienyl-py)Mes$_2$ (Compound 9)

2-(benzothienyl)pyridine (0.42 g, 2.0 mmol) in THF (50 mL), n-BuLi (1.6 M in hexane, 1.25 mL, 2.0 mmol), and BMes$_2$F (0.6 g, 2.0 mmol) were reacted by the procedure outlined above. Yellow crystals of compound 9 were obtained (0.56 g, 61%); $^1$H NMR (CD$_2$Cl$_2$): δ=8.65 (d, J=5.6 Hz, 1H), 8.04 (d, J=7.6 Hz, 1H), 7.98-7.89 (m, 2H), 7.66 (d, J=8.0 Hz, 1H), 7.35-7.27 (m, 2H), 7.18 (t, J=6.6 Hz, 1H), 6.68 (s, 4H), 2.18 (s, 6H), 1.90 (s, 12H); $^{13}$C NMR (CD$_2$Cl$_2$): δ=155.6, 146.1, 146.0, 141.4, 141.2, 140.3 134.5, 134.1, 130.4, 126.9, 126.2, 125.8, 125.4, 125.0, 123.8, 120.4, 118.5, 24.9, 20.7; $^{11}$B NMR (CD$_2$Cl$_2$): δ=7.96; HRMS (M)$^+$: Calcd for C$_{31}$H$_{30}$BNS, 459.2192. Found: 459.2198; Anal. Calcd for C$_{31}$H$_{30}$BNS: C, 81.04; H, 6.58; N, 3.05. Found: C, 81.68; H, 6.81; N, 2.99.

Example 5E

Synthesis of 3-(dimesitylboryl)-1-phenyl-2-(pyridine-2-yl)-indole (Compound 10)

To a solution of 1-phenyl-2-(pyridine-2-yl)-indole (0.54 g, 2.0 mmol) in THF (50 mL), at −78°, n-BuLi (1.6 M in hexane, 1.25 mL, 2.0 mmol) was added slowly and mixed for 45 min at −78°. Then, a THF solution (20 mL) of $BMes_2F$ (0.6 g, 2.0 mmol) was added slowly using a cannula and stirred overnight. Solvents were removed under reduced pressure and the resulting solid was dissolved in $CH_2Cl_2$ and quenched with 10 mL $H_2O$. The organic layer was separated and dried over $MgSO_4$ and filtered. After $CH_2Cl_2$ was removed under reduced pressure, the residue was purified over silica gel by flash column chromatography using $CH_2Cl_2$/hexanes mixture (1:1) to give a bright yellow powder, which was recrystallized from THF/hexanes to give yellow crystals of 1 (0.40 g, 39%). HREI-MS (M)$^+$: Anal. Calcd for $C_{37}H_{35}BN_2$, 518.2893. Found: 518.2901. Anal. Calcd for $C_{37}H_{35}BN_2$: C, 85.71; H, 6.80; N, 5.40. Found: C, 85.58; H, 6.62; N, 5.29. $^1H$ NMR ($CD_2Cl_2$): δ 8.54 (d, 1H, $^3J$=6.0), 7.82 (d, 1H, $^3J$=8.0), 7.65-7.61 (m, 3H), 7.57-7.54 (m, 1H), 7.48-7.47 (m, 2H), 7.18-7.17 (m, 2H), 7.05-7.02 (m, 1H), 7.00-6.97 (m, 1H), 6.83 (d, 1H, 3J=8.0), 6.66 (s, 4H), 2.16 (s, 6H), 1.94 (s, 12H). $^{13}C$ NMR ($CD_2Cl_2$): δ 151.8, 147.2, 145.6, 140.4, 140.2, 138.2, 136.5, 134.1, 130.1, 129.1, 128.5, 128.2, 124.8, 124.4, 120.7, 119.0, 117.1, 111.1, 25.0, 20.7. $^{11}B$ NMR ($C_6D_6$): δ 8.34.

Example 5F

Synthesis of bnzOxzPhB (Compound 11)

To a solution of 2-(2-bromophenyl)benzoxazole (1.15 g, 4.19 mmol) in THF (50 mL), at −78° C., n-BuLi (1.6 M in hexane, 2.63 mL, 4.2 mmol) was added slowly and mixed for 60 min at −78° C. Then, a THF solution (30 mL) of $BMes_2F$ (1.26 g, 4.2 mmol) was added slowly using a cannula and stirred overnight. Solvent was removed under reduced pressure and the resulting solid was dissolved in $CH_2Cl_2$ and quenched with 10 mL $H_2O$. The organic layer was separated and dried over $MgSO_4$ and filtered. After $CH_2Cl_2$ was removed under reduced pressure, the residue was purified over silica gel by flash column chromatography using $CH_2Cl_2$/hexanes mixture (1:4) to give a white powder, which was recrystallized from $CH_2Cl_2$/hexanes to give colorless crystals (0.68 g, 40.5%). HREI-MS (M)$^+$: Anal. Calcd for $C_{31}H_{30}BNO$, 443.2420. Found: 443.2432. $^1H$ NMR ($CD_2Cl_2$): δ 7.99 (d, 1H, $^3J$=7.0), 7.85 (d, 1H, $^3J$=7.5), 7.76 (d, 1H, $^3J$=8.0), 7.65 (d, 1H, $^3J$=7.5), 7.50-7.37 (m, 4H), 6.69 (s, 4H), 2.19 (s, 6H), 1.91 (s, 12H). $^{13}C$ NMR ($CD_2Cl_2$): δ 169.8, 153.2, 134.6, 134.4, 133.4, 131.8, 130.1, 127.1, 126.3, 126.2, 124.1, 123.2, 117.2, 112.8, 111.3, 25.4, 20.8. $^{11}B$ NMR ($CD_2Cl_2$): δ 3.43.

Example 5G

Synthesis of bnzTzPhB (Compound 12)

To a solution of 2-(2-bromophenyl)benzothiazole (1.45 g, 5.0 mmol) in THF (50 mL), at −78° C., n-BuLi (1.6 M in hexane, 3.2 mL, 5.0 mmol) was added slowly and mixed for 60 min at −78° C. Then, a THF solution (30 mL) of $BMes_2F$ (1.5 g, 5.0 mmol) was added slowly using a cannula and stirred overnight. Solvents were removed under reduced pressure and the resulting solid was dissolved in $CH_2Cl_2$ and quenched with 10 mL $H_2O$. The non-aqueous organic layer was separated and dried over $MgSO_4$ and filtered. After $CH_2Cl_2$ was removed under reduced pressure, the residue was purified over silica gel by flash column chromatography using $CH_2Cl_2$/hexanes mixture (1:4) to give a yellow powder, which was recrystallized from $CH_2Cl_2$/hexanes to give yellow crystals (1.4 g, 61.0%). HREI-MS (M)$^+$: Anal. Calcd for $C_{31}H_{30}BNS$, 459.2192. Found: 459.2209. $^1H$ NMR ($CD_2Cl_2$): δ 7.97-7.92 (m, 2H), 7.88 (t, 2H, $^3J$=7.5), 7.49-7.40 (m, 3H), 7.33 (t, 1H, $^3J$=7.5), 6.69 (s, 4H), 2.20 (s, 6H), 1.89 (s, 12H).
$^{13}C$ NMR ($CD_2Cl_2$): δ 175.5, 145.7, 134.5, 133.4, 132.7, 132.4, 130.5, 130.3, 128.5, 126.2, 126.0, 124.2, 124.0, 120.2, 25.0, 20.8. $^{11}B$ NMR ($CD_2Cl_2$): δ 4.48.

Example 5H

Synthesis of 5-$BMes_2$-(Benzofuryl-Py)$BMes_2$ (13)

To a solution of 2-(benzofuran-2-yl)-5-bromopyridine (0.55 g, 2.0 mmol) in THF (50 mL), at −78° C., n-BuLi (1.6 M in hexane, 2.5 mL, 4.0 mmol) was added slowly and mixed for 60 min at −78° C. Then, a THF solution (30 mL) of $BMes_2F$ (1.2 g, 4.0 mmol) was added slowly using a cannula and stirred overnight. Solvents were removed under reduced pressure and the resulting solid was dissolved in $CH_2Cl_2$ and quenched with 10 mL $H_2O$. The non-aqueous layer was separated and dried over $MgSO_4$ and filtered. After $CH_2Cl_2$ was removed under reduced pressure, the residue was purified over silica gel by flash column chromatography using $CH_2Cl_2$/hexanes mixture (1:9) to give a yellow powder, which was recrystallized from $CH_2Cl_2$/hexanes to give yellow crystals (0.71 g, 51%). HRESI-MS (M+H)$^+$: Anal. Calcd for $C_{49}H_{51}B_2NO$, 692.4235. Found: 692.4255. $^1H$ NMR ($CD_2Cl_2$): δ 8.71 (s, 1H), 8.10 (d, 1H, 3J=8.0), 7.98 (d, 1H, $^3J$=8.0), 7.78 (d, 1H, $^3J$=8.0), 7.66 (d, 1H, $^3J$=8.4), 7.46 (t, 1H, $^3J$=7.6), 7.33 (t, 1H, $^3J$=7.2), 6.96 (s, 4H), 6.75 (s, 4H), 2.49 (s, 6H), 2.36 (s, 6H), 2.19-1.69 (m, 24H). $^{13}C$ NMR ($CD_2Cl_2$): δ 161.1, 156.5, 153.3, 152.5, 150.9, 148.5, 143.0, 140.9, 140.1, 139.8, 135.0, 134.6, 130.7, 130.5, 129.0, 127.1, 124.7, 123.8, 115.4, 112.5, 24.7, 23.5, 21.4, 20.9. $^{11}B$ NMR ($CD_2Cl_2$): δ 7.38.

Example 5I

Synthesis of 5-$BMes_2$-(Benzothienyl-Py)$BMes_2$ (Compound 14)

To a solution of 2-(benzo[b]thiophen-2-yl)-5-bromopyridine (0.23 g, 0.78 mmol) in THF (50 mL), at −78° C., n-BuLi (1.6 M in hexane, 0.98 mL, 1.56 mmol) was added slowly and mixed for 60 min at −78° C. Then, a THF solution (30 mL) of $BMes_2F$ (0.47 g, 1.56 mmol) was added slowly using a cannula and stirred overnight. Solvents were removed under reduced pressure and the resulting solid was dissolved in $CH_2Cl_2$ and quenched with 10 mL $H_2O$. The organic layer was separated and dried over $MgSO_4$ and filtered. After $CH_2Cl_2$ was removed under reduced pressure, the residue was purified over silica gel by flash column chromatography using $CH_2Cl_2$/hexanes mixture (1:9) to give a yellow powder, which was recrystallized from $CH_2Cl_2$/hexanes to give yellow crystals (0.23 g, 42%). $^1H$ NMR ($C_6D_6$): δ 9.00 (s, 1H), 8.52 (d, 1H, $^3J$=8.5), 7.69 (d, 1H, $^3J$=8.5), 7.64 (d, 1H, $^3J$=8.0), 7.18 (t, 1H, $^3J$=7.5), 7.06 (t, 1H, $^3J$=7.3), 7.02 (d, 1H, $^3J$=8.0), 6.85 (s, 4H), 6.82 (s, 4H), 2.31 (s, 6H), 2.29 (s, 6H), 2.15 (s, 12H), 1.99 (s, 12H). $^{13}C$ NMR ($C_6D_6$): δ 157.2, 155.3, 147.6, 146.8, 142.6, 141.0, 140.4, 139.9, 135.6, 134.4, 134.1, 131.1, 129.3, 128.4, 126.8, 125.6, 123.8, 117.6, 23.6, 21.4, 21.0. $^{11}$B NMR (C$_6$D$_6$): δ 8.44.

Example 6

Crystal Structures

X-Ray crystal structures of the organoboron compounds described herein have been determined by single-crystal X-ray diffraction analysis and are shown in FIG. 2. Boron centers in these molecules have an approximately tetrahedral geometry. B—C bond lengths were in the range of 1.62 Å to 1.66 Å, while the B—N bond lengths were in the range of 1.65 to 1.67 Å, which are similar to those of BMes$_2$(ppy), and support that these molecules are highly sterically congested around the boron centers.

Example 7

Absorption and Fluorescence Spectra

Absorption spectra of the organoboron compounds described herein in toluene are shown in FIGS. 3-11. Absorption and fluorescence data are summarized in Table 1. These compounds are also luminescent in the solid state and in a polymer matrix. For each spectrum, an intense absorption band at 340-450 nm region is assigned to a charge transfer transition from the mesityl group to the N,C-chelate backbone. Consistent with the more electronegative furan ring, this transition appears at a lower energy for compound 1 compared to that of compound 2. Both compounds fluoresce with a blue color when irradiated by UV light. Emission maxima for compounds 1 and 2 are at 450 nm and 459 nm, respectively. Compound 1 is a much brighter emitter than compound 2, with an emission quantum efficiency two times of that of compound 2.

Example 8

Photoisomerization

Example 8A

Photoisomerization in Solution

Organoboron compounds 1 and 2 readily undergo photoisomerization in solution upon irradiation by UV light, changing color from colorless to deep blue as shown by FIGS. 5A-8B. For compound 1, an intense broad absorption band appears at $\lambda_{max}$=580 nm upon irradiation, while for compound 2, a similar absorption band appears at $\lambda_{max}$=590 nm. This isomerisation is fully reversible thermally, as established by NMR spectral studies.

The photoisomerization process for both compounds was monitored by $^1$H NMR spectra showing 100% conversion of compound 1 to 1a and of compound 2 to 2a. The structures of the dark-colored isomers for both compounds was determined to be 1a and 2a, respectively, as shown in FIG. 1B, similar to the dark-colored isomer of B(ppy)Mes$_2$.

Example 8B

Bulk Photoisomerization of Compound 10 to 10a for Obtaining Crystals of Compound 10a Bulk photoisomerization of compound 10 (5 mg) to 10a was carried out in distilled hexanes in a schlenk flask. To exclude any oxygen, 3 cycles of freezing, pumping and thawing were performed using liquid N$_2$. Then, the flask was irradiated at 365 nm in a UV reactor at ambient temperature. The colorless solid of compound 10 has poor solubility in hexanes and displays very bright emission at 490 nm. While compound 10 (about 10 mg in 5 mL of toluene) appeared insoluble in hexanes initially, there was neither precipitate nor any emission after 1.5 days of irradiation. After irradiating the solution for 2 days, the volume of dark turquoise-green solution was reduced to about 10 mL of its original volume in vacuo. After standing at −50° C. for a month, dark turquoise-green crystals were formed and isolated from this solution. These dark crystals of compound 10a are very soluble in hexanes, paraffin oil and grease at room temperature. To prevent the crystals from being re-dissolved, the solution was decanted immediately after the flask was retrieved from the fridge, before the temperature was increased to ambient temperature. A single crystal was then quickly covered by epoxy glue to prevent decomposition in the air during mounting of the crystal. $^{11}$B NMR in C$_6$D$_6$: δ −4.55 ppm for 10a.

Example 8C

Bulk Photoisomerization Rates and Quantum Efficiencies

For practical applications, it is highly desirable for a photochromic compound to undergo fast conversion from its colorless state to its dark state with a high quantum efficiency. To compare the performance of organoboron compounds described herein with B(ppy)Mes$_2$, the relative rates of bulk photoisomerization of these compounds were determined by $^1$H NMR spectroscopy using B(ppy)Mes$_2$ as an internal standard. Data for this study are presented in Table 1 for all of the compounds in FIG. 1. A comparison of two of the compounds is provided below.

Under the same irradiation conditions and at the same concentration, compound 2 was found to undergo much faster photoisomerization than B(ppy)Mes$_2$ with a relative rate of 3.4 (2 versus B(ppy)Mes$_2$), whereas compound 1 was much slower with a relative rate of 0.2 (1 versus B(ppy)Mes$_2$). Both compounds 1 and 2 have a much greater absorption at the irradiation wavelength than B(ppy)Mes$_2$ (ε=~2630 M$^{-1}$ cm$^{-1}$ for B(ppy)Mes$_2$, ~7000 M$^{-1}$ cm$^{-1}$ for compound 1, ~7300 M$^{-1}$ cm$^{-1}$ for compound 2, at 365 nm). Hence, compound 1 has a much lower photoisomerization quantum efficiency than that of B(ppy)Mes$_2$ and compound 2. Surprisingly, compound 2 has a lower quantum efficiency than B(ppy)Mes$_2$, despite its greater photoisomerization rate, due to the greater absorbance of compound 2 at its excitation wavelength. To accurately determine the photoisomerization quantum efficiency of compound 1, photoisomerization quantum efficiency measurements were measured for both B(ppy)Mes$_2$ and compound 2 using ferrioxalate actinometry. Photoisomerization quantum yields of compound 2 and B(ppy)Mes$_2$ were found to be 0.75 (standard deviation 2) for compound 2 and 0.85 (standard deviation 2) for B(ppy)Mes$_2$. This confirmed that compound 2 not only undergoes fast isomerization but also has a high quantum efficiency. Based on this data, it is believed that compound 2 is a better candidate for certain photochromic applications compared to compound 1.

Example 10

Thermal Reversal

For certain applications, following conversion to its dark colored state, it is desirable to return a photochromic material to its original colorless state so that it can be used repeatedly. In certain other applications, such as UV sensing and/or UV blocking, a photochromic material should exhibit sufficient thermal stability in its dark colored state so that it does not interfere with the sensing process and maximizes the efficiency of UV blocking. Thus, thermal reversal processes of photochromic materials are important. Thermal stability of dark isomers of the organoboron compounds of FIG. 1 were studied using NMR spectroscopic methods. Data for the dark colored isomers of these compounds are shown in Table 1. The dark isomers of compounds 1 and 2 were found to have good thermal stability with little change after being kept at 50° C. for about 10 hrs. At elevated temperatures (>50° C.), the dark colored isomers of both compounds were converted to their colorless isomers. This data further supports that these photochromic organoboron compounds are suitable for UV sensing and/or UV blocking applications.

Example 11

Photoisomerization in Polymer Matrices

Photochromic compounds 1 and 2 have been shown to undergo fast photoisomerization in a polymer matrix. The polymer matrices studied included poly(dimethylsiloxane) ("PDMS"), polystyrene ("PS"), poly(methyl methacrylate) ("PMMA"), and poly(ethylene-co-vinyl alcohol) ("EVOH"). When each of compounds 1 and 2 were doped into the polymer matrix, the resulting polymeric films were colorless. However, upon UV irradiation (by a hand-held UV lamp), the colorless polymeric films underwent a rapid color change to dark blue or dark purple within minutes. UV-Vis spectra confirmed that these color changes were caused by photoisomerization of the photochromic compound dye in the polymer matrix in the same manner as was seen in solution. As a representative sample, UV-Vis spectral change of compound 2 in a polystyrene matrix is shown in FIG. 5A.

In further studies, compounds 2 and 8 were chosen as representatives of the photochromic organoboron compounds and were doped into PS and PMMA to form polymeric films. UV-Vis absorption spectra were measured on a Varian UV-Vis spectrometer. See FIGS. 5A-8B for data collected during these studies.

PS film was prepared as follows: compound 2 (0.70 mg) and PS (200 mg) were dissolved in 1 mL of $CH_2Cl_2$, 0.5 mL of which was carefully placed and dried inside the horizontal surface of a quartz cuvette. PS films with higher concentrations of compound 2 (1.40 mg, 2.10 mg) were also prepared in the same manner. The thickness of these films was less than 0.2 mm and was kept constant for all films, though the exact film thickness was not determined. PS film doped with compound 8 was prepared in the same way as described above. PS films doped by 0.50 mg, 1.60 mg, and 2.40 mg of compound 8 were prepared and examined.

PMMA films was prepared in the same way as the PS films, except that compound 2 and PMMA were dissolved in chloroform. PMMA films doped by 0.93 mg, 1.19 mg, and 2.10 mg of compound 2 were prepared and examined. Compound 8 in PMMA film was prepared in the same way. PMMA films doped by 0.808 mg, 1.67 mg, 2.90 mg of compound 8 were prepared and examined.

Example 12

Oxygen Sensing

The dark colored isomers of photochromic compounds of general formula (A), (B), (C), (D) or (E) are highly sensitive to oxygen. Exposure to oxygen causes a rapid disappearance of the dark color. In solution, the dark color disappears within minutes when the flask is left open to air (about 5 mg compound in 2.5 g polymer). In a polymer matrix that is doped with a compound of general formula (A), (B), (C), (D) or (E), the ability of oxygen to penetrate the polymer matrix is dependent on which polymer matrix has been selected. PDMS has the highest oxygen permeability. As a result, PDMS that has been doped with a photochromic compound of general formula (A), (B), (C), (D) or (E) has a fast response to oxygen exposure. That is, in some embodiments the dark-colored isomer loses substantially all of its color within approximately 30 minutes, and all of its color after 60 min. EVOH is the least easily penetrated by oxygen; therefore embodiments of doped organoboron compounds as described herein do not change color even after weeks and months of exposure to air. PS that is doped with a compound of general formula (A), (B), (C), (D) or (E) is penetrable by oxygen, and in some embodiments the dark-colored isomer loses its color after about 2 weeks of air exposure.

Polymeric films comprising compound 2 and PS were prepared by spin coating 4 mL of a toluene solution of compound 2 (1.0 mg with 100 mg of PS) on 1.0 cm×3.0 cm quartz glass substrate. Films were carefully dried at room temperature for 5 hrs under reduced pressure to remove residue solvent. UV-Vis spectral change of the dark colored isomer of 2 in polystyrene upon exposure to air was observed and is shown in FIG. 4. The response time of PDMS films toward oxygen is in general much faster than polystyrene due to the highly porous structure of PDMS. However, the dark colored isomer appears to have a greater chemical stability in polystyrene than in PDMS. Because the photochromic boron compounds are also highly fluorescent, they can be used to sense oxygen molecules in the fluorescence mode. Fluorescence of compound 2 in polystyrene undergoes a dramatic fluorescence quenching after being converted to its C—C coupled product in the polymer matrix (UV irradiation, followed by exposure to oxygen.)

Example 13

UV-Blocking Test

Films of compound 2 in EVOH were prepared and tested for photochromic switching and to determine the stability of the dark colored isomer inside EVOH under ambient conditions. It was observed that EVOH films comprising compound 2 underwent rapid photoisomerization and color change to dark blue upon irradiation by light. This dark color of the EVOH films remained for weeks without exhibiting any degradation under air at ambient temperature.

This stability may be due to EVOH's known very low permeability for oxygen (Lee, S. K.; Okura, I., Analytical Communications, 1997, 34, 185; Cox, M. E. J. Polym. Sci.: Part A: Polym Chem. 1986, 24, 621; Okaya, T.; Ikari, K. in Polyvinyl Alcohol Developments, Finch, C. A. ed., John Wiley&Sons, New York, 1992, p 195; Foster R. H. in Coating Technology Handbook, Satas, D. ed., Marcel Dekker Inc, New York, 1991, p 399.). For these reasons, EVOH is a likely substrate for incorporating a photochromic compound as described herein for UV-blocking, for example, for food packaging.

Example 14

Synthesis and Photoisomerization of Compounds 15 and 16

General Procedure. Diethyl ether ($Et_2O$) was used directly from the Pure Solv™ Solvent Purification System (Innovative Technology Inc., Amesbury, Mass., U.S.A.). All reactions were carried out under ultra pure nitrogen atmosphere, using Schlenk and vacuum line techniques. $^1$H and $^{13}$C NMR spectra were recorded on a Bruker Avance 300, 400 or 500 MHz spectrometer. UV-Vis spectra were recorded on a Varian UV-Visible spectrometer.

1. Synthetic procedure for 1-Me (Compound 16).

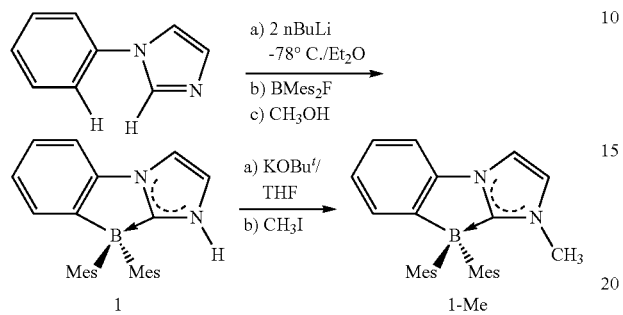

n-Butyllithium (2.5 M, 1.7 mL, 4.2 mmol) was slowly added to a solution of 1-phenylimidazole 1 (0.3 g, 2.1 mmol) in Et$_2$O (100 mL) at −78° C. The solution was warmed to room temperature and stirred for 3 hours. Then a diethyl ether solution of dimesitylboron fluoride (0.62 g, 2.1 mmol) was added dropwise at −78° C. The resulting solution was slowly warmed to room temperature and stirred overnight. After addition of excess methanol, the solution was concentrated under vacuum. Further purification by chromatography on silica gel (hexane/CH$_2$Cl$_2$) gave compound 1 as a white solid residue, which was recrystallized from hexane/DCM (0.4 g, 50%). $^1$H NMR (CDCl$_3$, 25° C., ppm): 9.07 (s), 7.66 (d, 1H, J=7.0 Hz), 7.40 (d, 1H, J=2.0 Hz), 7.29 (d, 1H, J=8.5 Hz), 7.21 (t, 1H, J=8.5 Hz), 7.15-7.31 (t, 1H, J=7.0 Hz), 6.87 (d, 1H, J=1.5 Hz), 6.70 (s, 4H), 2.23 (s, 6H), 1.88 (s, 12H). $^{13}$C NMR (CDCl$_3$, 25° C., ppm): 140.2, 140.2, 134.7, 133.1, 129.0, 126.7, 124.9, 120.0, 111.6, 110.3, 77.3, 77.0, 76.8, 24.9, 20.7. $^{11}$B NMR (CDCl$_3$, 25° C., ppm): −9.66 (s). Elemental Analysis, Calcd for C$_{27}$H$_{30}$BN$_2$: C, 82.44; H, 7.69; N, 7.12. Found: C, 82.58; H, 7.49; N, 7.09.

Compound 1 (100 mg, 0.25 mmol) and potassium t-butyl oxide (40 mg, 0.35 mmol) were dissolved in 5 ml THF in a vial, and excess methane iodine (0.5 ml) was then added to the solution. The resulting solution was stirred overnight at room temperature, with white precipitate generated during the progress of the reaction. After filtration of the salt and condensation of the clear solution under vacuum, 1-Me (compound 16) was obtained almost quantitatively and was crystallized from hexane/DCM. $^1$H NMR (CD$_2$Cl$_2$, 25° C., ppm): 7.60 (d, 1H, J=7.5 Hz), 7.52 (d, 1H, J=1.5 Hz), 7.33 (d, 1H, J=7.5 Hz), 7.18 (td, 1H, $^3$J=7.5 Hz, $^4$J=1.5 Hz), 7.09 (td, 1H, $^3$J=7.5 Hz, $^4$J=1.5 Hz), 7.00 (d, 1H, J=1.5 Hz), 6.66 (s, 4H), 3.57 (s, 6H), 2.20 (s, 6H), 1.83 (s, 12H). $^{11}$B NMR (CDCl$_3$, 25° C., ppm): −9.75 (s).

2. Synthetic Procedure for 2-Me (Compound 15).

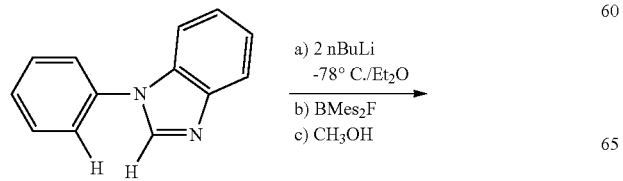

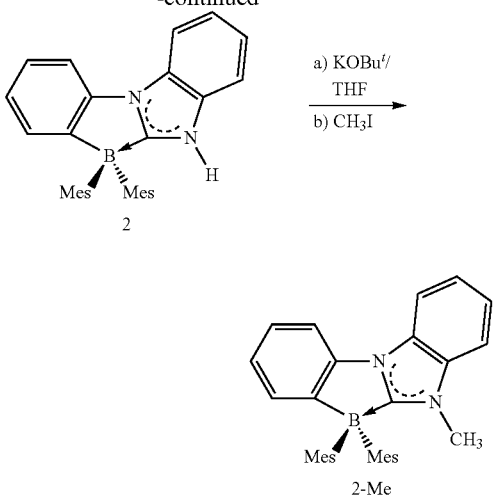

The precursor 1-phenyl-benzimidazole was synthesized according to a literature procedure (Verma, A. K. et al., Tetrahedron Lett. 2007, 48: 4207). Compound 2 was synthesized and further purified the same way as outlined for compound 1 above, then recrystallized from hexane/DCM (0.21 g, 30%). $^1$H NMR (CD$_2$Cl$_2$, 25° C., ppm): 9.69 (s), 8.15 (d, 1H, J=10.8 Hz), 7.84 (d, 1H, J=8.4 Hz), 7.58-7.66 (m, 3H), 7.49 (t, 1H, J=10 Hz), 7.37 (t, 1H, J=10 Hz), 7.23 (t, 1H, J=10 Hz), 6.87 (s, 4H), 2.21 (s, 6H), 1.92 (s, 12H). $^{11}$B NMR (CD$_2$Cl$_2$, 25° C., ppm): −9.65(s).

2-Me (compound 15) was obtained almost quantitatively in the same way as 1-Me above, and was crystallized from hexane/DCM. 2-Me: $^1$H NMR (CD$_2$Cl$_2$, 25° C., ppm): 8.20 (d, 1H, J=7.5 Hz), 7.81 (d, 1H, J=8.0 Hz), 7.68 (d, 1H, J=7.5 Hz), 7.61 (td, 1H, $^3$J=6.0 Hz, $^4$J=2.0 Hz), 7.56-7.60 (m, 2H), 7.30 (t, 1H, J=7.5 Hz), 7.13 (t, 1H, J=7.0 Hz), 6.69 (s, 4H), 3.57 (s, 6H), 2.21 (s, 6H), 1.88 (s, 12H). $^{11}$B NMR (C$_6$D$_6$, 25° C., ppm): −8.98 (s).

Figure 13:
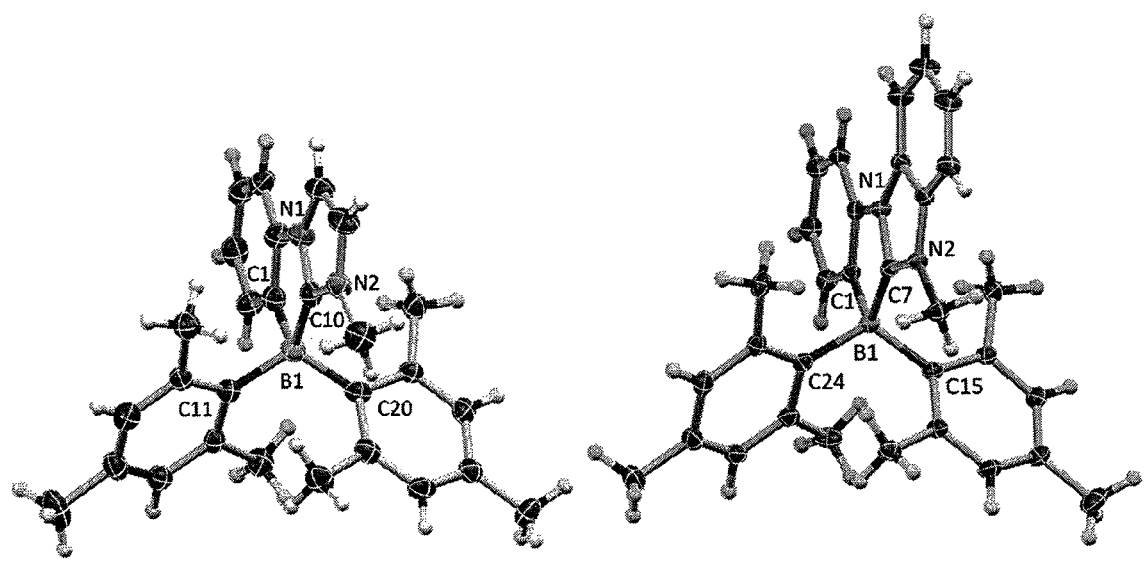
FIG. 13 shows X-ray crystallographic structures for compound 16 (left) and compound 15 (right) determined by single-crystal X-ray diffraction analysis.

Crystal structures of 1-Me (compound 16) and 2-Me (compound 15) were determined and are shown in FIG. 13.

3. Photoisomerization of 1-Me (Compound 16) and 2-Me (Compound 15).

Figure 14A:
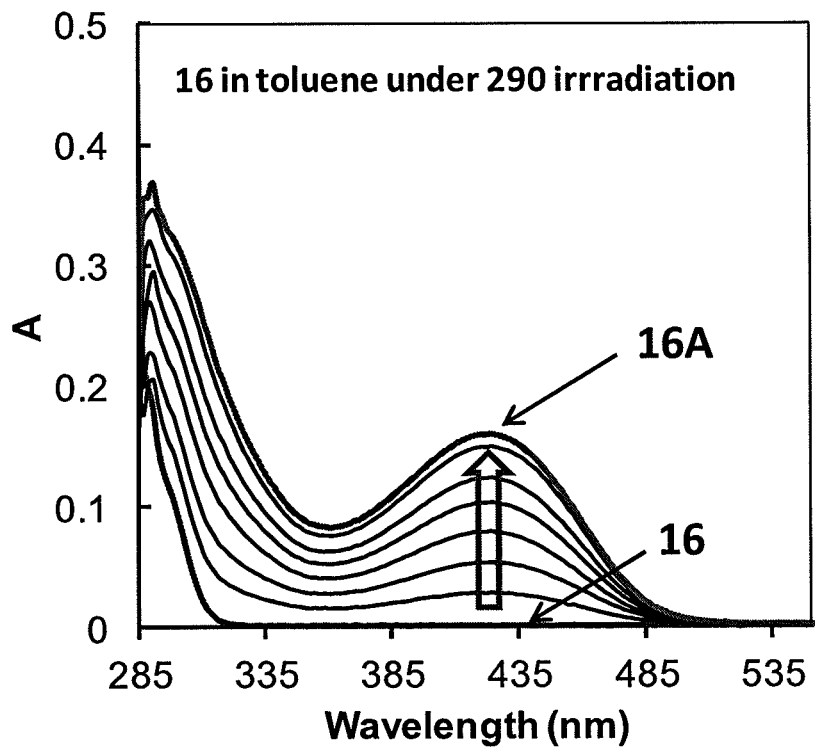
FIG. 14A is a plot of absorbance (A) versus wavelength showing UV-vis spectral changes recorded for compound 16 in toluene upon exposure to UV light (290 nm).
Figure 14B:
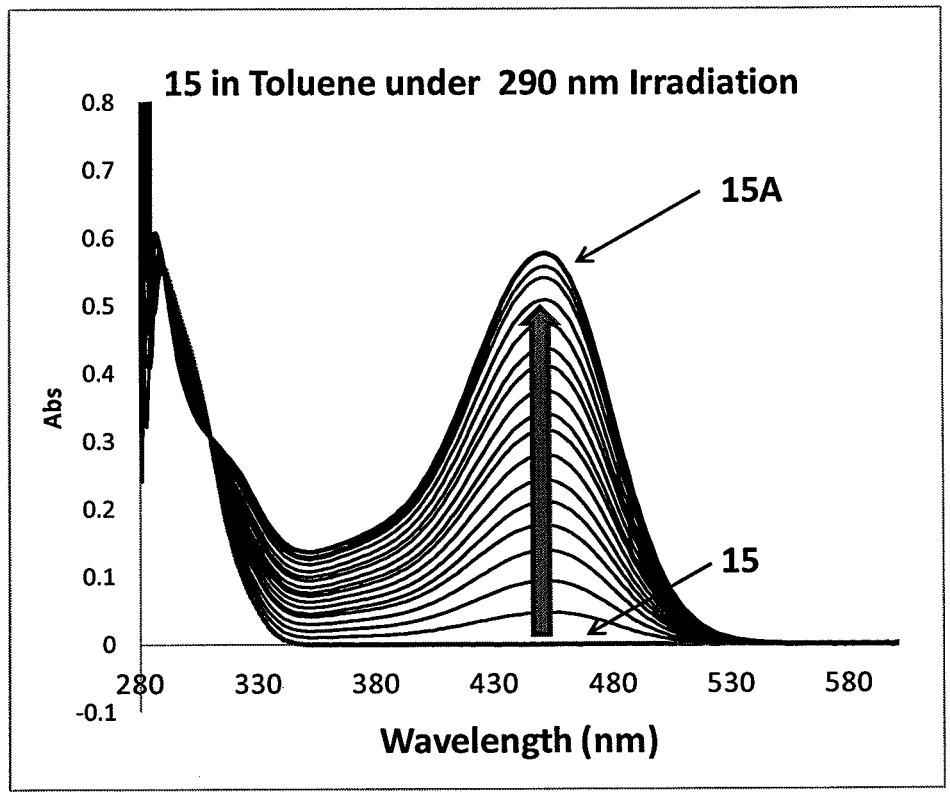
FIG. 14B is a plot of absorbance (Abs) versus wavelength showing UV-vis spectral changes recorded for compound 15 in toluene upon exposure to UV light (290 nm).

Photoisomerization of compounds 15 and 16 was carried out in the same manner as for other compounds with the exception that the excitation energy used was 290 nm. The structural change from compounds 15 and 16 to the corresponding isomers of 15A and 16A is shown in the scheme below. The UV-Vis absorption spectral change in toluene is shown in FIG. 14.

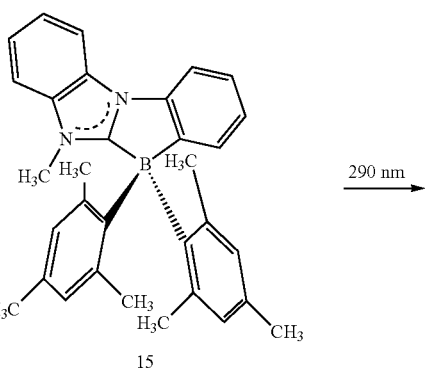

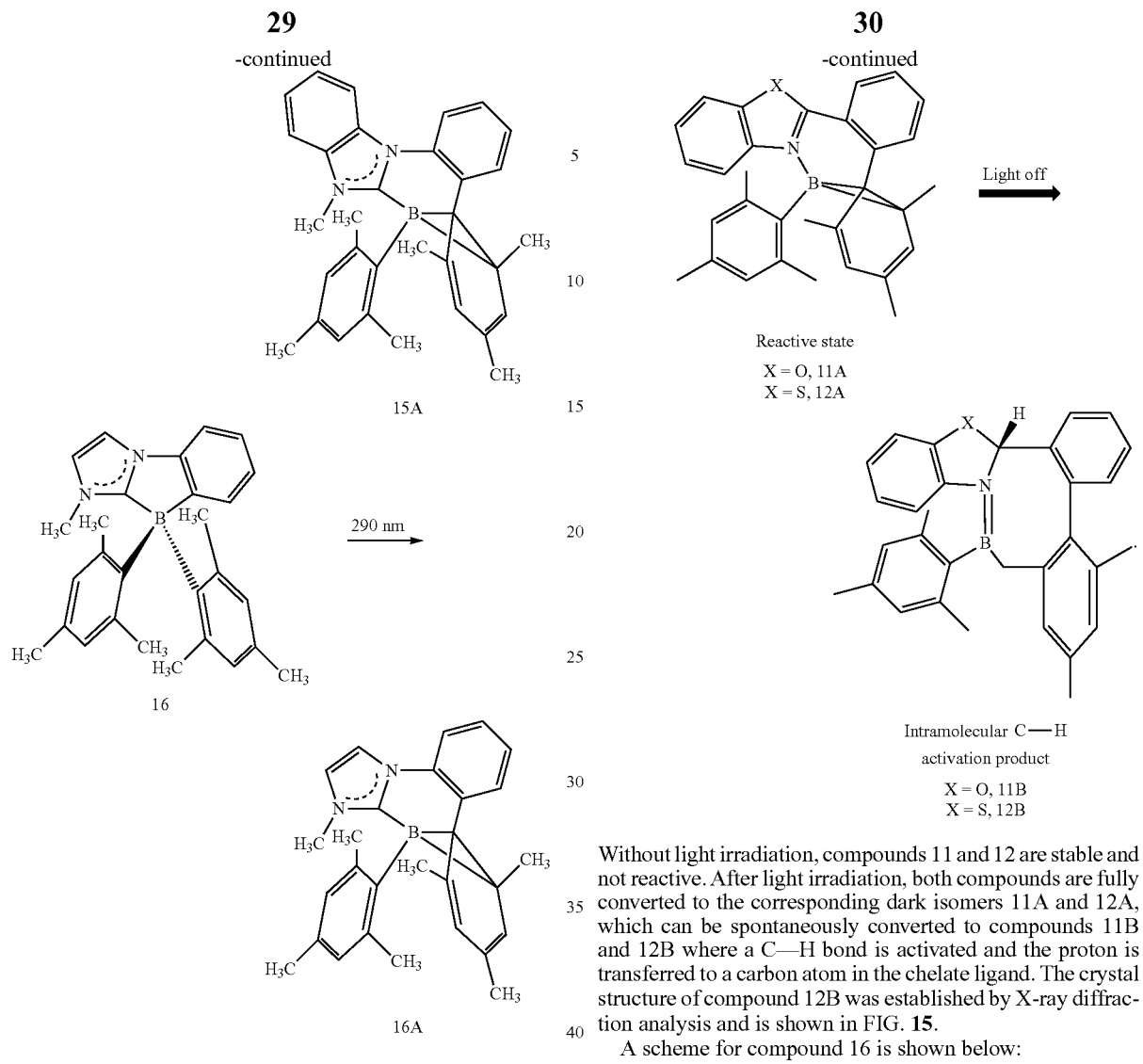

Example 15

Control of Reactivity of Compounds Using Light

In some embodiments, reactivity of compounds of the invention is controlled by light. This was demonstrated for compounds 11, 12 and 16.

Figure 15:
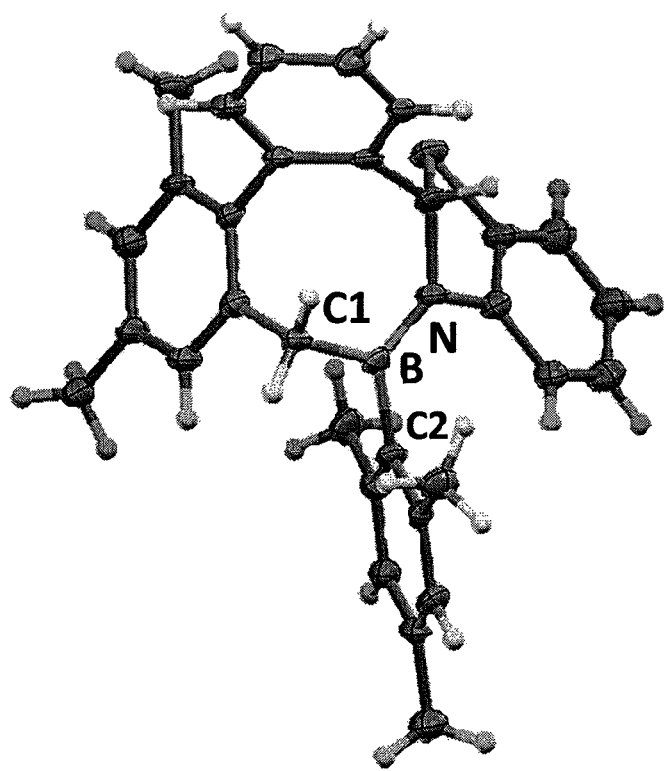
FIG. 15 shows the crystal structure of compound 12B determined by X-ray diffraction analysis.

A scheme showing that the reactivity of compounds 11 and 12 can be controlled by light is shown below:

Without light irradiation, compounds 11 and 12 are stable and not reactive. After light irradiation, both compounds are fully converted to the corresponding dark isomers 11A and 12A, which can be spontaneously converted to compounds 11B and 12B where a C—H bond is activated and the proton is transferred to a carbon atom in the chelate ligand. The crystal structure of compound 12B was established by X-ray diffraction analysis and is shown in FIG. 15.

A scheme for compound 16 is shown below:

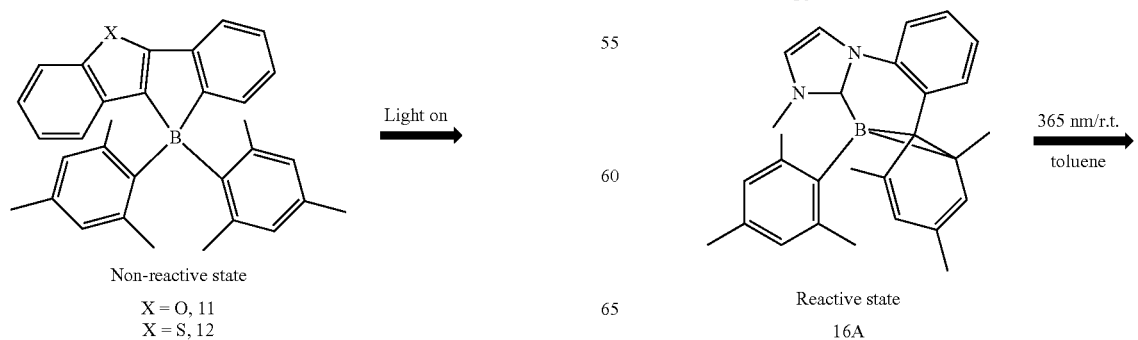

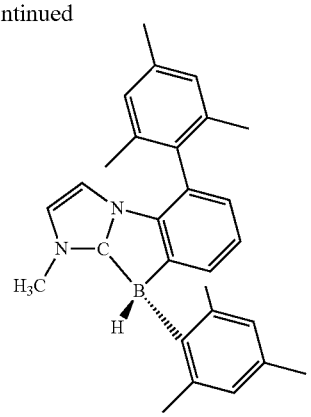

Intramolecular C—H
activation product
16B

Figure 16:
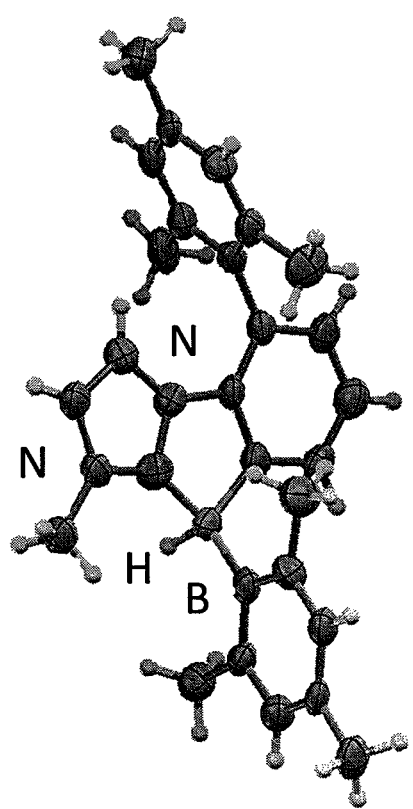
FIG. 16 shows the crystal structure of compound 16B determined by X-ray diffraction analysis.

Compound 16 is stable under air and ambient light. When irradiated by UV light at 290 nm or 300 nm, it changes color to bright orange, forming the isomer 16A. Species 16A is an air-stable compound but can be very reactive when irradiated by light, transforming to a new species 16B. This stepwise transformation controlled by light is useful in, e.g., light-controlled chemical reactions and transformation. Species 16B was characterized by crystal structure, which is shown in FIG. 16. Compound 15 undergoes a similar transformation.

It will be understood by those skilled in the art that this description is made with reference to certain preferred embodiments and that it is possible to make other embodiments employing the principles of the invention which fall within its spirit and scope as defined by the claims.

We claim:

1. A compound of general formula (A):

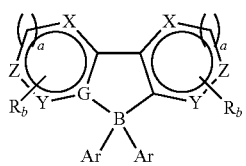

(A)

wherein B is boron;
G is nitrogen, sulfur, substituted or unsubstituted carbon, or oxygen;
a is zero or one, and a for the ring containing G is not equal to the other a;
X, Y and Z are independently oxygen, sulfur, substituted or unsubstituted nitrogen, or substituted or unsubstituted carbon;
Ar is independently a subsituted or unsubstituted aromatic moiety wherein at least one of the two Ar moieties is a bi-, tri-, tetra-, or penta-substituted aromatic moiety that has substitutents located in the two ortho positions relative to the boron-Ar bond;
R is a substituent; and
b is a number from 0 to 5;
wherein at least one of G, X, Y and Z is oxygen, sulfur, or substituted or unsubstituted nitrogen, and wherein substituents are selected from aliphatic groups, alkoxyl, silyl, siloxyl, aryl, B(aliphatic)(aryl), B(aryl)$_2$, or any combination thereof, wherein a substituent may be further substituted, and wherein two substituents can join to form a fused aryl ring.

2. The compound of claim 1, wherein:
(i) X is carbon, and at least one of Z and Y is oxygen, sulfur, or substituted or unsubstituted nitrogen;
(ii) one of X, Y and Z is nitrogen, one of X, Y and Z is carbon, and one of X, Y and Z is sulfur or oxygen;
(iii) one of X, Y and Z is nitrogen, and two of X, Y and Z are carbon;
(iv) X is oxygen or sulfur, and both Y and Z are carbon;
(v) one of X, Y and Z is carbon, and two of X, Y and Z are nitrogen; or
(vi) X, Y and Z are each nitrogen.

3. The compound of claim 1, wherein the compound of general formula (A) is:

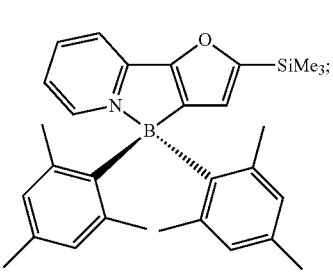

compound 1

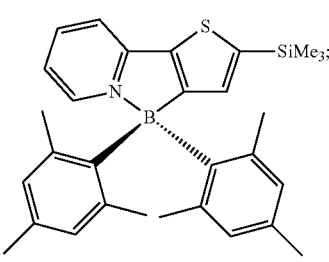

compound 2

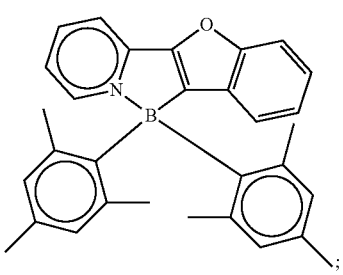

compound 8

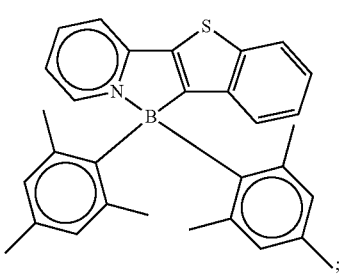

compound 9

-continued compound 10

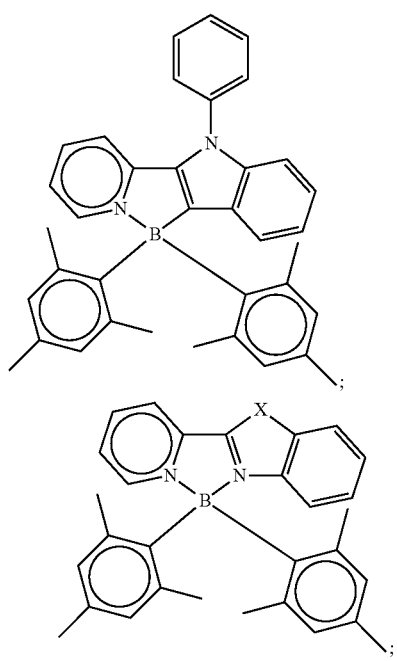

compound 11 (X = O);
compound 12 (X = S)

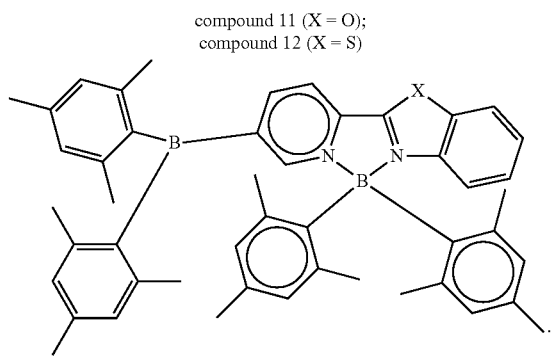

compound 13 (X = O); or
compound 14 (X = S)

4. The compound of claim 1, wherein Ar is 1,3,5-mesityl.
5. The compound of claim 1, wherein R is B(mesityl)$_2$.
6. The compound of claim 1, wherein G is carbon.
7. A compound of general formula (B):

(B)

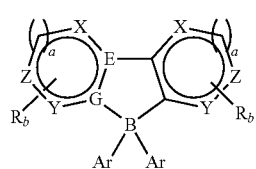

wherein B is boron;
G is nitrogen, sulfur, substituted or unsubstituted carbon, or oxygen;
a is zero or one, and a for the ring containing G is not equal to the other a;
X, Y and Z are independently oxygen, sulfur, substituted or unsubstituted nitrogen, or substituted or unsubstituted carbon;
E is substituted or unsubstituted nitrogen or substituted or unsubstituted carbon;
Ar is independently a subsituted or unsubstituted aromatic moiety wherein at least one of the two Ar moieties is a bi-, tri-, tetra-, or penta-substituted aromatic moiety that has substitutents located in the two ortho positions relative to the boron-Ar bond;
R is a substituent; and
b is a number from 0 to 5;
wherein at least one of G, X, Y and Z is oxygen, sulfur, or substituted or unsubstituted nitrogen, and
wherein substituents are selected from aliphatic groups, alkoxyl, silyl, siloxyl, aryl, B(aliphatic)(aryl), B(aryl)$_2$, or any combination thereof, wherein a substituent may be further substituted, and wherein two substituents can join to form a fused aryl ring.

8. The compound of claim 7, wherein G is carbon.
9. The compound of claim 7, wherein G is carbon, E is nitrogen, Y in the ring containing G is nitrogen, and Y in the other ring is carbon.
10. The compound of claim 7, wherein a is 0; or wherein a is 1 in the ring containing G, and a is 0 in the other ring.
11. The compound of claim 7, wherein b is 1 in the ring containing G, and b is 0 in the other ring.
12. The compound of claim 7, wherein b is 3 in the ring containing G; and b is 0 in the other ring or two substituents join together to form a fused aryl ring.
13. The compound of claim 7, wherein Ar is 1,3,5-mesityl.
14. The compound of claim 7, wherein the compound of general formula (B) is:

compound 15

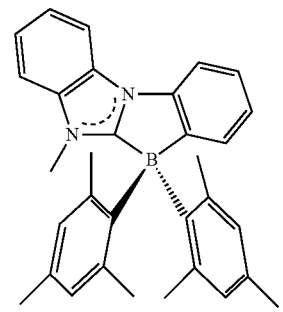

or compound 16

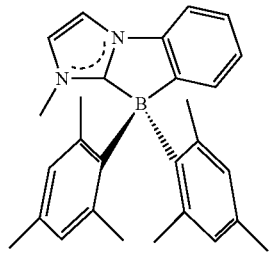

15. A compound of general formula (C):

(C)

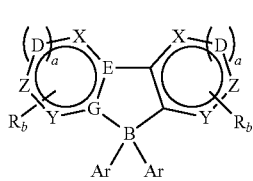

wherein B is boron;
G is nitrogen, sulfur, substituted or unsubstituted carbon, or oxygen;
D is substituted or unsubstituted nitrogen, sulfur, substituted or unsubstituted carbon, or oxygen;

a is zero or one, and a for the ring containing G is not equal to the other a;

X, Y and Z are independently oxygen, sulfur, substituted or unsubstituted nitrogen, or substituted or unsubstituted carbon;

E is substituted or unsubstituted nitrogen or substituted or unsubstituted carbon;

Ar is independently a subsituted or unsubstituted aromatic moiety wherein at least one of the two Ar moieties is a bi-, tri-, tetra-, or penta-substituted aromatic moiety that has substitutents located in the two ortho positions relative to the boron-Ar bond;

R is a substituent; and b is a number from 0 to 5;

wherein at least one of G, X, Y and Z is oxygen, sulfur, or substituted or unsubstituted nitrogen, and wherein substituents are selected from aliphatic groups, alkoxyl, silyl, siloxyl, aryl, B(aliphatic)(aryl), B(aryl)$_2$, or any combination thereof, wherein a substituent may be further substituted, and wherein two substituents can join to form a fused aryl ring.

16. The compound of claim 7, which is a compound of general formula (D):

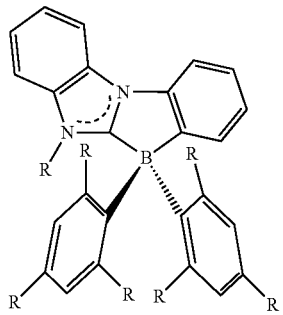

(D)

wherein R is H, alkyl, aryl, or BAr$_2$.

17. The compound of claim 15, which is a compound of general formula (E):

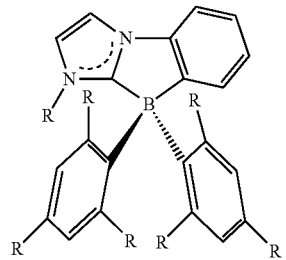

(E)

wherein R is H, alkyl, aryl, or BAr$_2$.

18. The compound of claim 17, wherein R is methyl and the compound is:

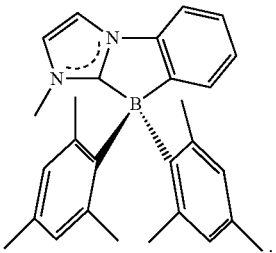

16

19. The compound of claim 1, wherein the compound is photochromic, or wherein the compound's reactivity is controlled or transformed when irradiated by light.

20. A method of making a compound of general formula (A) of claim 1, comprising:
reacting a chelate ligand in a toluene solution at about −78° C. with either n-butyl lithium or lithium di(isopropyl) amide;
adding BAr$_2$halo; and
warming the solution to ambient temperature.

* * * * *